US012630524B2

(12) United States Patent
Paukner et al.

(10) Patent No.: US 12,630,524 B2
(45) Date of Patent: May 19, 2026

(54) PLEUROMUTILIN IN DERIVATIVES FOR TREATING VIRAL INFECTIONS

(71) Applicant: ARIVA MED GMBH, Vienna (AT)

(72) Inventors: Susanne Paukner, Vienna (AT); Rosemarie Riedl, Vienna (AT); Wolfgang Wicha, Bruck an der Leitha (AT)

(73) Assignee: ARIVA MED GMBH, Vienna (AT)

( * ) Notice: Subject to any disclaimer, the term of this patent is extended or adjusted under 35 U.S.C. 154(b) by 725 days.

(21) Appl. No.: 17/919,204

(22) PCT Filed: Apr. 16, 2021

(86) PCT No.: PCT/EP2021/059904

§ 371 (c)(1),
(2) Date: Oct. 14, 2022

(87) PCT Pub. No.: WO2021/209596

PCT Pub. Date: Oct. 21, 2021

(65) Prior Publication Data

US 2023/0174509 A1 Jun. 8, 2023

(30) Foreign Application Priority Data

Apr. 17, 2020 (EP) .................................... 20170074

(51) Int. Cl.

| | |
|---|---|
| ***C07D 401/12*** | (2006.01) |
| ***A61P 31/04*** | (2006.01) |
| ***A61P 31/14*** | (2006.01) |
| ***C07D 241/04*** | (2006.01) |

(52) U.S. Cl.

CPC ............ *C07D 401/12* (2013.01); *A61P 31/04* (2018.01); *A61P 31/14* (2018.01); *C07D 241/04* (2013.01)

(58) Field of Classification Search

None

See application file for complete search history.

(56) References Cited

FOREIGN PATENT DOCUMENTS

| | | | |
|---|---|---|---|
| CN | 103242210 | A | 8/2013 |
| CN | 103204787 | B | 10/2014 |
| WO | 2008113089 | A1 | 9/2008 |
| WO | 2009106839 | A1 | 9/2009 |
| WO | 2011146954 | A1 | 12/2011 |
| WO | 2015110481 | A1 | 7/2015 |
| WO | 2016202788 | A1 | 12/2016 |

OTHER PUBLICATIONS

Lindsley et. al. "Distribution of Airborne Influenza Virus and Respiratory Syncytial Virus in an Urgent Care Medical Clinic" CID, 2010, 50, 5, 693-698. DOI: 10.1086/650457 (Year: 2010).*

Tiamulin (CAS 55297-95-5) CAS Registry File Accessed Jun. 13, 2025 from STN, entered into STN Nov. 16, 1984 (Year: 1984).*

Chen et al., "Preventive Effects of Valnemulin on Lipopolysaccharide-Induced Acute Lung Injury in Mice," Inflammation, vol. 33, No. 5, pp. 306-314 (2010).

Berner et al., "Synthese ab-trans-anellierter derivate des tricyclischen diterpens pleuromutilin durch intramolekulare 1,5-hydrid-verschiebung," Tetrahedron, vol. 36, pp. 1807-1811 (1980).

Hafner et al., "Anti-inflammatory activity of lefamulin versus azithromycin and dexamethasone in vivo and in vitro in a lipopolysaccharide-induced lung neutrophilia mouse model," Plos One, https://doi.org/10.1371/journal.pone.0237659 (2021).

Matthay et al., "The acute respiratory distress syndrome," Journal of Clinical Investigation, vol. 122, No. 8, pp. 2731-2740 (2012).

(Continued)

*Primary Examiner* — Jennifer A Berrios
*Assistant Examiner* — Sophia Reilly
(74) *Attorney, Agent, or Firm* — Venable LLP

(57) ABSTRACT

A compound selected from 14-O-[((Alkyl-, cycloalkyl-, heterocycloalkyl-, heteroaryl-, or aryl)-sulfanyl)-acetyl]-12-epi-mutilins, or 14-O-[((Alkyl-, cycloalkyl-, heterocycloalkyl-, heteroaryl-, or aryl)-oxy)-acetyl]-12-epi-mutilins, wherein 12-epi-mutilin is characterized in that the mutilin ring at position 12 is substituted by two substituents, the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom and all other substituents of the mutilin ring having the same stereochemistry compared with the stereochemistry of the substituents at the corresponding positions in the naturally occurring pleuromutilin ring; optionally in the form of a pharmaceutically acceptable salt and/or solvate, prodrug or metabolite, wherein the naturally occurring pleuromutilin is of formula.

PLEU

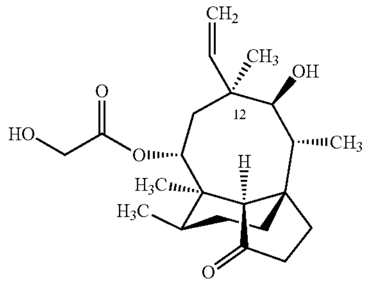

for the specific use in the treatment or prevention of a disease mediated by a virus. The invention further relates to 12-epi-12-desvinyl-14-O-[(Piperidin-4-ylsulfanyl]-acetyl]-12-[2-(3-methyl-pyrazin-2-yl)-ethenyl]-mutilin and its therapeutic uses.

22 Claims, 3 Drawing Sheets

(56) References Cited

OTHER PUBLICATIONS

Matute-Bello et al., "Animal models of acute lung injury," American Journal of Physiology Lung Cellular and Molecular Physiology, vol. 295, No. 3, pp. L379-L399 (2008).
Giacalone et al., "Neutrophil Adaptations upon Recruitment to the Lung: New Concepts and Implications for Homeostasis and Disease," International Journal of Molecular Sciences, vol. 21, 851, pp. 1-21 (2020).
Yu et al., "Itaconate: An emerging determinant of inflammation in activated macrophages," Immunology & Cell Biology, vol. 97, pp. 134-141 (2019).
Liao et al., "4-Octyl itaconate inhibits aerobic glycolysis by targeting GAPDH to exert anti-inflammatory effects," Nature Communications, vol. 10, No. 5091, pp. 1-11 (2019).
Long et al., "The Cfr rRNA Methyltransferase Confers Resistance to Phenicols, Lincosamides, Oxazolidinones, Pleuromutilins, and Streptogramin A Antibiotics," Antimicrobial Agents and Chemotherapy, vol. 50, No. 7, pp. 2500-2505 (2006).
Mendes et al., "Low Prevalence of Gram-Positive Isolates Showing Elevated Lefamulin MIC Results during the SENTRY Surveillance Program for 2015-2016 and Characterization of Resistance Mechanisms," Antimicrobial Agents and Chemotherapy, vol. 63, No. 4, e02158-18, pp. 1-9 (2019).
Q1 2020 Nabriva Therapeutics PLC Earnings Call of May 11, 2020, Press release (https://investors.nabriva.com/news-releases/news-release-details/nabriva-therapeutics-reports-first-quarter-2020-financial), downloaded May 28, 2020.
Alexander et al., "Oral Lefamulin vs Moxidloxacin for Early Clinical Response Among Adults with Community-Acquired Bacterial Pneumonia—The LEAP 2 Randomized Clinical Trial," Journal of American Medical Association, vol. 322, No. 17, pp. 1661-1671 (2019).
Zuo et al., "Antibacterial Activity and Pharmacokinetic Profile of a Promising Antibacterial Agent: 22-(2-Amino-phenylsulfanyl)-22-Deoxypleuromutilin," Molecules, vol. 25, No. 878, pp. 1-13 (2020).
Asheshov, et al., "A Survey of Actinomycetes for Antiphage Activity," Antibiotics & Chemotherapy, vol. 4, No. 4, pp. 380-394 (1954).
Alarcon, et al., "Screening for new compounds with anitherpes activity," Antiviral Research, vol. 4, pp. 231-243 (1984).
"Pleuromutilin," The Merck Index, 12th edition, Item 7694, p. 1298.
Zhang, et al., "Valnemulin downregulates nitric oxide, prostaglandin E2, and cytokine production via inhibition of NF-KB and MAPK activity," International Immunopharmacology, vol. 9, pp. 810-816 (2009).

* cited by examiner

PLEUROMUTILIN IN DERIVATIVES FOR TREATING VIRAL INFECTIONS

CROSS REFERENCE TO RELATED APPLICATIONS

The present application is a national-stage entry under 35 U.S.C. § 371 of International Patent Application No. PCT/EP2021/059904, published as WO 2021/209596A1, filed Apr. 16, 2021, which claims priority to EP 20170074.7, filed Apr. 17, 2020, the entire disclosure of each of which is hereby incorporated by reference.

BACKGROUND OF THE INVENTION

Field of the Invention

The present invention relates to a novel Pleuromutilin and novel therapeutic use of Pleuromutilins.

Pleuromutilin, a compound of formula (pleuromutilin)

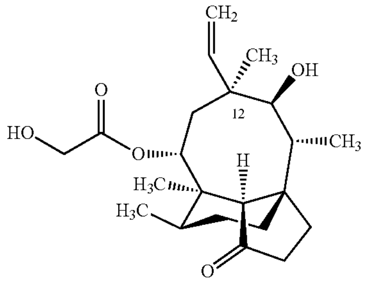

is a naturally occurring antibiotic, produced e.g. by the basidiomycetes *Pleurotus mutilus* and *P. passeckerianus*, see e.g. The Merck Index, 12th edition, item 7694.

A number of further pleuromutilins having the principle ring structure of pleuromutilin and being substituted at the primary hydroxy group have been developed, e.g. as antibacterials. Due to their pronounced antibacterial activity, a group of pleuromutilin derivatives, amino-hydroxy-substituted cyclohexylsulfanylacetylmutilins, as disclosed in WO 2008/113089, have been found to be of particular interest. As described in WO 2008/113089 14-O-{[(4-Amino-2-hydroxy-cyclohexyl)-sulfanyl]-acetyl}-mutilins are particularly useful compounds because of their activity against Gram-positive and Gram-negative bacteria.

In WO 2015/110481 A1 Pleuromutilin derivatives are disclosed which are called “12-epi-mutilins”. The term “12-epi-mutilin” means that the mutilin ring at position 12 is substituted by two substituents, the first substituent at position 12 of the mutilin ring is a methyl group which methyl group has the inverse stereochemistry compared with the stereochemistry of the methyl group at position 12 of the naturally occurring pleuromutilin ring, the second substituent at position 12 of the mutilin ring is a hydrocarbon group comprising at least one nitrogen atom, and all other substituents of the mutilin ring having the same stereochemistry compared with the stereochemistry of the substituents at the corresponding positions in the naturally occurring pleuromutilin ring; optionally in the form of a salt and/or solvate, in particular in the form of a salt. A first synthetic approach towards the inverted stereochemistry was described by Berner, H. et al (Berner, H.; Schulz, G.; Schneider H. *Tetrahedron* 1980, 36, 1807-1811).

In WO 2015/110481 A1, certain of these 12-epi-mutilin compounds have been found to show interesting activity against Gram-positive and Gram-negative bacteria.

Pharmaceutical active compounds derived from pleuromutilin (semi synthetic compounds) are inhibitors of ribosomal protein synthesis in bacteria. Representatives of semi-synthetic pleuromutilins for human use are Retapamulin (approved as AltargoP®, AltabaxP®), a topical agent approved for short term treatment of impetigo and infected small lacerations, abrasions or sutured wounds, and Lefamulin (approved as Xenleta®) for the treatment of adults with community-acquired bacterial pneumonia (CABP). Tiamulin (Denagard®) and Valnemulin (Econor®) are two other semi-synthetic pleuromutilin derivatives which have been used systemically as antibiotics in veterinary medicine for many years.

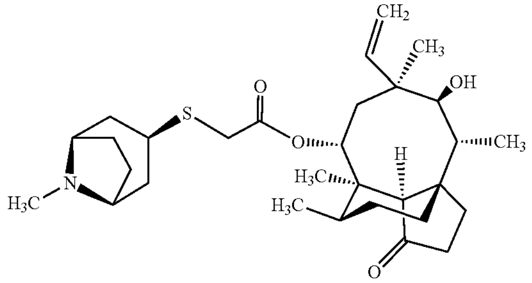

Retapamulin

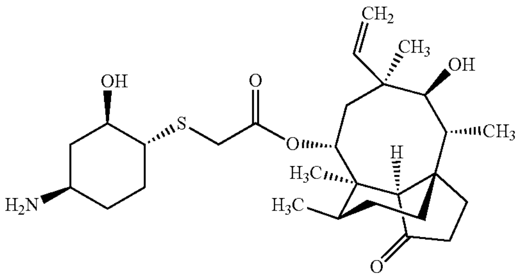

Lefamulin

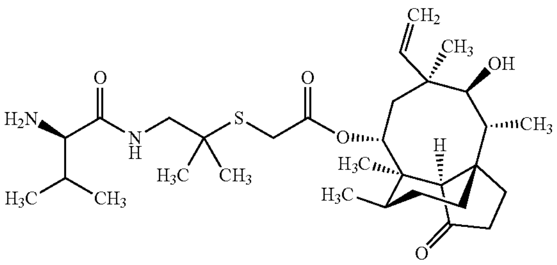

Valnemulin

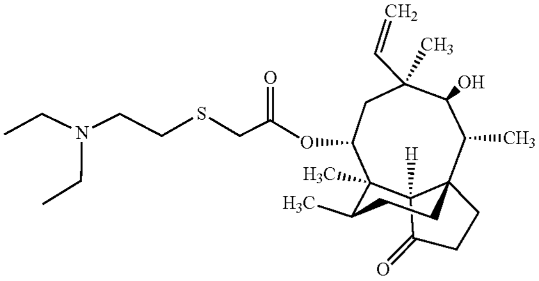

Tiamulin

Approved semisynthetic compounds derived from pleuromutilin have shown excellent activity against bacterial organisms which include inter alia *Streptococcus pneumoniae, Haemophilus influenzae, Staphylococcus aureus* (including MRSA), *Moraxella catarrhalis, Legionella pneumophila, Chlamydophila pneumoniae* and *Mycoplasma pneumoniae*.

Viral diseases are one of the leading causes of morbidity and mortality in the world. Respiratory viruses such as influenza, respiratory syncytial virus, certain adenoviruses, rhinoviruses and corona viruses and in particular the newly emerged severe acute respiratory syndrome coronavirus 2 (SARS-CoV-2; COVID-19) have a significant impact on public health.

In Asheshov, Igor N. et. al., Antibiotics & Chemotherapy 4/4 (1954), 380-394, for the first time the antiviral activity of pleuromutilins was described with antiviral activity of Pleuromutilin itself for an influenza A virus strain (PR8) at a concentration of 2 mg/mL. In contrast, Pleuromutilin did not show antiviral activity for polio virus in this study.

Furthermore, in Alacórn, Balbino et. al., Antiviral Research, 4 (1984), 231-243, the antiviral activity of Pleuromutilin against both, DNA and RNA viruses, in particular herpes simplex type 1 (HSV-1) virus at a test compound concentration that conferred a 50% protection of the cytopathic effect induced by HSV-1 (CPE50) of 40 μM (15 μg/mL) and activity against vesicular stomatitis virus (VSV) is described.

In WO 2009/106839 the use of Tiamulin as an antiviral agent is claimed, with effect of Tiamulin on influenza A virus, porcine reproductive and respiratory syndrome virus (PRRSV) type 1 and 2 in a viral up-take assay 4 hours post inoculation with the virus at tiamulin concentrations of 0.1-10 μg/mL compared to Valnemulin and the effect of Tiamulin on endosomal pH exemplified. Valnemulin did not exhibit antiviral activity and it was stated that other pleuromutilin antibiotics have not been found to have an effect on viruses.

Alteration of the endosomal or lysosomal pH by Tiamulin and associated prevention of fusion of the viral membrane with endo- and lysosomes, which is a pre-requisite for viral entry, was described as potential mode-of-action.

CN 103204787B and CN 103242210 both disclose further pleuromutilin derivatives and generally mention their use in antiviral drugs, without, however, disclosing any actual proof for an antiviral action.

Certain statements about potential antiviral and anti-inflammatory effects of Lefamulin were made in the "Q1 2020 Nabriva Therapeutics PLC Earnings Call" of May 11, 2020, (a transcript of which is available under www.yahoo.com/news/edited-transcript-nbrv-oq-earnings-144108621.html, downloaded Jun. 10, 2020 as well as in a press release of May 11, 2020 (investors.nabriva.com/news-releases/news-release-details/nabriva-therapeutics-reports-first-quarter-2020-financial), downloaded May 28, 2020.

SUMMARY OF THE INVENTION

Surprisingly, it was now found that the 12-epi mutilins as disclosed in WO 2015/110481 A1 are effective against viruses and, thus, effective against diseases mediated by viruses.

Therefore, in a first aspect the present invention relates to a compound as defined in claims 1 to 11 and 16, or a pharmaceutically acceptable salt, solvate, prodrug or metabolite thereof, for the specific use in the treatment or prevention of a disease mediated by a virus.

In a further aspect, the present invention relates to a method of treatment or prevention of a disease mediated by a virus, comprising administering a compound as defined in any of claims 1 to 11 and 16, or a pharmaceutically acceptable salt, solvate, prodrug or metabolite thereof to a subject in need of such treatment.

In yet a further aspect, the present invention relates to the compound of claims 11 and 16, respectively and to its use as a medicament as well as a specific use in the treatment of a disease mediated by bacteria, in particular Gram positive bacteria, and/or a disease mediated by a virus.

DETAILED DESCRIPTION OF THE INVENTION

Figure 1:
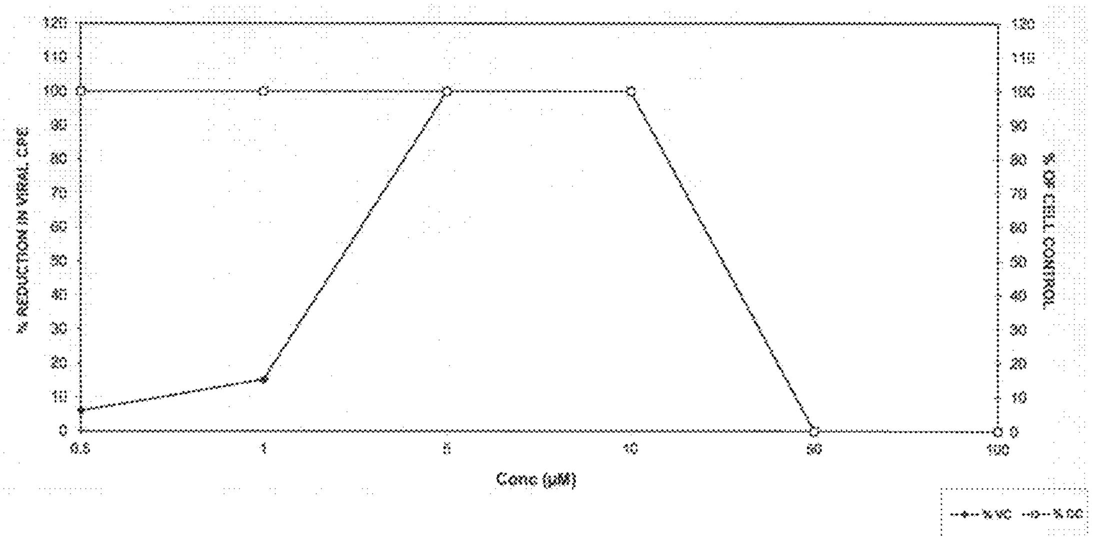
FIG. 1 demonstrates the effect of the compound of claim 16 (BC 9842) against alpha corona virus 229E (HCoV-229E) in MRC-5 cells 6 days post infections with the virus.
Figure 2:
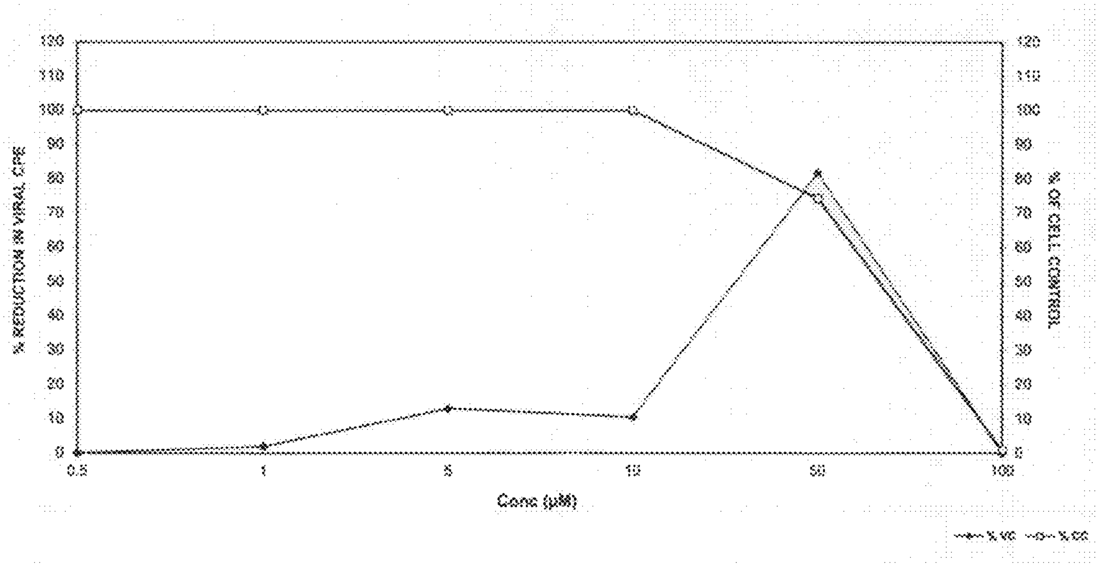
FIG. 2 demonstrates the effect of Tiamulin in the same assay.
Figure 3:
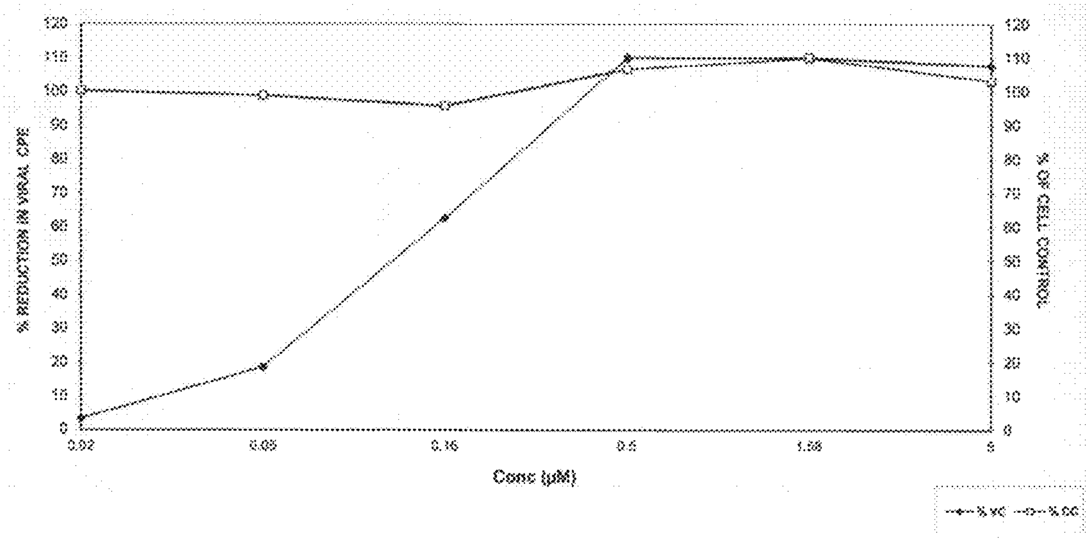
FIG. 3 demonstrates the effect of Remdesivir in the same assay.

The present invention refers to the treatment and prevention of a disease mediated by a virus, e.g. a viral disease or a viral infection. Treatment typically includes administering a compound as used according to the present invention to a subject in need thereof, i.e. a subject being diagnosed to have a disease mediated by a virus. Prevention of a disease mediated by a virus includes administering the compounds before onset of disease symptoms. Prevention may be considered after a subject has been infected with a virus but has not shown any symptoms, or wherein a subject has been exposed and/or is prone to exposition to a virus.

The results of the experiments show that besides its antibacterial activity, the 12-epi-mutilin BC 9842 is also actively reducing the cytopathic effect mediated by different viruses. This antiviral effect was particularly shown for such viruses that are characterized in that they are positive- or negative sense single-stranded RNA viruses, in particular, enveloped positive- or negative sense single-stranded RNA viruses (such as Coronaviridae, Paramyxoviridae, Orthomyxoviridae, and Flaviviridae). Moreover, some of the investigated viruses, including measles virus are known for a transmission involving the respiratory route, in particular airborne transmission. Corona virus and Respiratory Syncytial Virus also cause infections of the respiratory tract in humans.

In a preferred embodiment of the present invention, the virus is a positive- or negative-sense single-stranded RNA virus, preferably the virus is selected from the group consisting of Coronaviridae including in particular human coronavirus, Paramyxoviridae including in particular Paramyxovirinae, such as Measles virus, and Pneumovirinae, such as Respiratory Syncytial Virus, Orthomyxoviridae including in particular Influenza virus, Flaviviridae including in particular Dengue virus and Zika virus, and Picornaviridae including in particular Rhinovirus.

In an other embodiment, the disease is an airborne disease. An airborne disease is mediated by a virus transmitted by the air.

Viral infections can affect various organs. In a preferred embodiment of the present invention, the disease is a respiratory disease, including upper and lower respiratory infections, in particular lower respiratory infections.

In particular, the disease is an acute respiratory syndrome, such as Influenza, Severe Acute Respiratory Syndrome (SARS), Middle East Respiratory Syndrome (MERS) or COVID-19.

In a further embodiment of the present invention the disease is mediated by a virus selected from the group consisting of viruses of the virus families Coronaviridae, in particular a corona virus such as SARS-CoV, SARS-CoV2, MERS-CoV or HCoV-229E, Orthomyxoviridae, in particular an Influenza virus such as Influenza A and B viruses, Paramyxoviridae in particular Respiratory Syncytial Virus and Adenoviridae, in particular Adenovirus.

In one embodiment, the virus is a corona virus, in particular selected from the group consisting of SARS-CoV, SARS-CoV2, MERS-CoV, and HCoV-229E as well as mutations thereof. Such corona viruses are known to cause (severe) acute respiratory syndromes, such as SARS, MERS or COVID-19.

The compounds used according to the present invention are generally known from WO 2015/110481 A1, the disclosure of which is incorporated herein by reference. Especially the compounds used according to the present invention can be synthesized according to the preparation methods disclosed in WO 2015/110481 A1. Alternatively, a synthetic approach via 14-O-chloroacetyl-12-epi-mutilin is available as described in the co-pending application (PCT/EP2021/059885).

In a further aspect, the present invention relates to a novel 12-epi-mutilin of formula II (II)

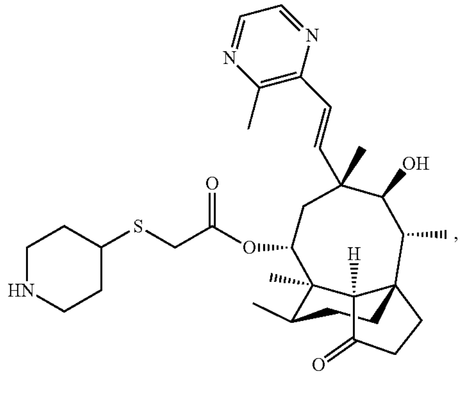

optionally in form of a pharmaceutically acceptable salt, in particular the dihydrochloride salt and/or solvate.

The systematic name of this compound is 12-epi-12-desvinyl-14-O-[(Piperidin-4-ylsulfanyl]-acetyl]-12-[2-(3-methyl-pyrazin-2-yl)-ethenyl]-mutilin. In the following, this compound is also referred to as "BC 9842".

This compound is novel and has surprisingly good efficacy both against the microbes as generally disclosed in WO 2015/110481 (MICs≤2 μg/mL against *Staphylococcus aureus* ATCCC 49951 and MICs≤16 μg/mL against *Escherichia co/i* ATCC 25922) and against viruses (Examples 2 to 5). In particular, BC 9842 has a MIC (minimum inhibitory concentration) of ≤0.03 μg/mL against *Staphylococcus aureus* ATCC49951 and *Streptococcus pneumoniae* ATCC49619 (Example 6). Moreover, BC 9842 has shown good metabolic stability in mouse and human primary hepatocytes e.g. of >60% and of >20% parent compound, respectively (Example 7).

Thus, the invention also relates to BC 9842, optionally in the form of a pharmaceutically acceptable salt, for use as a medicament.

In a further aspect, the present invention provides BC 9842 for use in the treatment and prevention of a disease mediated by bacteria.

In one embodiment, the disease is mediated by bacteria selected from the group consisting of Gram-positive bacteria including
- staphylococci, e.g. *Staphylococcus aureus,*
- streptococci, e.g. *Streptococcus pneumoniae*, ß-hemolytic or *viridans* group *Streptococcus* spp.,
- enterococci, e.g. *Enterococcus faecium,*
- Peptostreptococci, e.g. *Peptostreptococcus anaerobius,*
- Clostridia, e.g. *Clostridium difficile* and *Clostridium perfringens,*
- as well as *Listeria monocytogenes, Eubacterium lentum, Finegoldia magna, Anaerococcus prevotii, Peptoniphilus assaccharolyticus*, and *Propionibacterium* spp.

and

Gram-negative bacteria including
- *Moraxella*, e.g. *Moraxella catarrhalis,*
- *Haemophilus*, e.g. *Haemophilus influenzae* and *Haemophilus parainfluenzeae,*
- Chlamydiae, e.g. *Chlamydophila pneumoniae* and *Chlamydia trachomatis*
- Neisseriaceae, e.g. *Neisseria gonorrhoeae,*
- *Mycoplasma* spp., e.g. *Mycoplasma pneumoniae* and *Mycoplasma genitalium,*
- Fusobacteria, e.g. *Fusobacterium fusiforme, Fusobacterium necrophorum, Fusobacterium mortiferum*, and *Fusobacterium varium,*
- *Prevotella* spp., e.g. *Prevotella buccae* and *Prevotella oris,*
- *Porphyromonas* spp., e.g. *Porphyromonas gingivalis* and *Porphyromonas asaccharolytica,*
- *Legionella*, e.g. *Legionella pneumophila,*
- as well as *Bacteroides fragilis*, and *Acinetobacter lwoffii.*

The disease may be mediated by Gram-negative or Gram-positive bacteria including aerobes, facultative anaerobes or obligatory anaerobes. In one embodiment, the disease is mediated by aerobic or facultative anaerobic bacteria, in particular aerobic or facultative anaerobic Gram-positive bacteria.

Preferably, the disease is mediated by bacteria selected from the group consisting of staphylococci and streptococci.

Individual bacterial phenotypes with resistance against pleuromutilin antibiotics (Long, K. S.; Poehlsgaard, J.; Kehrenberg, C.; Schwarz, S.; Vester, B. *Antimicrob Agents Chemother.* 2006, 50(7), 2500-2505) and Lefamulin (Mendes R E, Paukner S, Doyle T B, Gelone S P, Flamm R K, Sader H S. *Antimicrob Agents Chemother.* 2019 63(4), e02158-18) have been described. Potential acquired Lefamulin resistance mechanisms identified to date include the following (sorted by epidemiological relevance): i) target protection by ABC-F proteins e.g. vga(A-E) of *Staphy-*

*lococcus* spp., lsa(E) of *S. agalactiae, Enterococcus* spp., and *S. aureus*, sal(A) of coagulase-negative *Staphylococcus* spp., ii) Modification of the target e.g. Mutations in rplC and rplD genes encoding ribosomal proteins located outside of PTC, mutations in domain V of the 23S rRNA, or methylation of position A2503 of the 23S rRNA in the PTC mediated by the Cfr methyl transferase (encoded by cfr) (Paukner S, Riedl R. Pleuromutilins: Potent Drugs for Resistant Bugs-Mode of Action and Resistance. Cold Spring Harb Perspect Med. 2017 Jan. 3; 7(1):a027110. doi: 10.1101/cshperspect.a027110. PMID: 27742734; PMCID: PMC5204327).

In particular, the disease is mediated by bacteria resistant to Lefamulin. For example, bacteria having a resistance mechanism, e.g. mediated by vga(A), lsa(E) or cfr.

In a preferred embodiment, the disease is selected from the group consisting of

- a respiratory tract infection including pneumonia, e.g. a community-acquired bacterial pneumonia (CABP) and nosocomial pneumonia,
- an infection of skin and/or soft tissue including acute bacterial skin and skin structure infection (ABSSI),
- a systemic infection including sepsis,
- a prosthetic joint infection,
- sexually transmitted infections (STI) and
- acne.

More preferably, the disease is a respiratory tract infection including community-acquired pneumonia and nosocomial pneumonia, a skin and/or soft tissue infection including acute bacterial skin and skin structure infection, a sexually transmitted infection, or sepsis.

Moreover, the present invention relates to a method of treatment or prevention of a disease mediated by bacteria, comprising administering BC 9842 or a pharmaceutically acceptable salt, solvate, prodrug or metabolite thereof to a subject in need of such treatment.

Furthermore, the invention also relates to a pharmaceutical composition comprising BC 9842 optionally in the form of a pharmaceutically acceptable salt, in association with at least one pharmaceutical excipient, optionally further comprising another pharmaceutically active agent.

Treating, treatment or to treat as understood herein includes on one hand the complete curing, curation or to cure a condition (the infectious disease) such that it comes to its end and on the other hand also ameliorating, amelioration or to ameliorate a condition such that its symptoms are reduced at least partially or individually.

Preventing, prevention, or to prevent includes administering a compound before a condition is diagnosed or before onset of (all) disease symptoms of the condition. For example, prevention according to the present invention may be considered after a subject has been infected with a virus and/or bacteria but has not shown any symptoms of an infection (asymptomatic carrier) or, wherein a subject has been exposed and/or is prone to exposition to a virus and/or bacteria known for mediating, i.e. causing, a certain infectious disease. In one embodiment, the compound to be used according to the invention, in particular BC 9842 is administered to treat a viral infection itself and to prevent a co- and/or superinfection mediated by bacteria.

The appropriate dosage of the compound to be used according to the present invention, in particular BC 9842, will, of course, vary depending upon, for example, the individual host, the mode of administration and the nature and severity of the conditions being treated. However, in general, for satisfactory results in larger mammals, for example humans, an indicated daily dosage is in the range from about 0.5 mg to 3 g of a compound of the present invention or for use as to the present invention conveniently administered, for example, in divided doses up to four times a day.

The compound used according to the present invention may be administered by any conventional route, for example enterally, e.g. including nasal, buccal, rectal, oral administration; parenterally, e.g. including intravenous, intramuscular, subcutaneous administration; or topically, e.g. including pulmonary, epicutaneous, intranasal, intratracheal administration, e.g. in form of coated or uncoated tablets, capsules, injectable solutions or suspensions, e.g. in the form of ampoules, vials, in the form of ointments, creams, gels, pastes, inhaler powder, foams, tinctures, lip sticks, drops, sprays, or in the form of suppositories, e.g. in analogous manner to the antibiotic agent tobramycin or macrolides, such as erythromycins, e.g. clarithromycin or azithromycin.

Preferably, the compound used according to the present invention is administered via inhalation, via intravenous or subcutaneous injection, or orally.

The compound for use according to the present invention, in particular BC 9842, is in the free form or a pharmaceutically acceptable salt, solvate, prodrug or metabolite thereof. Preferably, the compound for use according to the present invention is in the free form, as defined by formula I or II, in the form of a pharmaceutically acceptable salt and/or in the form of a solvate.

The compound used according to the present invention, in particular BC 9842, may be administered in the form of a pharmaceutically acceptable salt, e.g. an acid addition salt, or in free form, optionally in the form of a solvate.

A salt of a compound used according to the present invention includes an acid addition salt. Pharmaceutically acceptable acid addition salts include salts of a compound of the present invention or used according to the present invention with an acid, e.g. hydrogen fumaric acid, fumaric acid, tartaric acid, ethane-1,2-disulphonic acid, maleic acid, naphthalin-1,5-sulphonic acid, acetic acid, malic acid, lactic acid e.g. L-lactic acid, succinic acid, salicylic acid, azelaic acid, 2-[(2,6-dichlorophenyl)amino]benzene acetic acid, hydrochloric acid, deuterochloric acid, preferably hydrochloric acid, acetic acid, L-lactic acid and maleic acid, more preferably hydrochloric acid.

In a preferred embodiment, BC 9842 is provided in the form of its dihydrochloride salt.

The compound used according to the present invention, in particular BC 9842, may be used for the pharmaceutical treatment contemplated herein alone or in combination with one or more other pharmaceutically active agents. Such other pharmaceutically active agents include e.g. other antiviral agents. Such other antiviral agents may preferably be selected from the group consisting of nucleoside and nucleotide analogues and RNA polymerase inhibitors, e.g. remdesivir or ribavirin, viral protease inhibitors such as lopinavir or ritonavir, viral neuraminidase inhibitors, such as oseltamivir, and other agents used in antiviral therapy such as hydroxychloroquine, interferons (interferon alfa and/or beta), or other broad-spectrum antiviral agents.

In one embodiment, BC 9842 may be used for pharmaceutical treatment according to the present invention alone or in combination with one or more other pharmaceutically active agents Such other pharmaceutically active agents include e.g. other antibiotics and anti-inflammatory agents, and, if used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

A pharmaceutical composition comprising a compound used according to the present invention, in particular BC 9842, may in addition comprise at least one pharmaceutically acceptable excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

Such pharmaceutical compositions may be manufactured according, e.g. analogously, to a method as conventional, e.g. by mixing, granulating, coating, dissolving, spray drying or lyophilizing processes. Unit dosage form may contain, for example, from about 0.5 mg to about 3000 mg, such as 10 mg to about 600 mg.

A subject in need of a treatment as contemplated by the present invention may be any living subject suffering from a disease mediated by a virus, i.e. a viral infection, and/or in case of the use of BC 9842 suffering from a disease mediated by bacteria, i.e. a bacterial infection. Especially, the subject may be a human or an animal.

EXAMPLES

The trivial name mutilin refers to the IUPAC systematic name (1S,2R,3S,4S,6R,7R,8R,14R)-3,6-dihydroxy-2,4,7,14-tetramethyl-4-vinyl-tricyclo[5.4.3.01,8]tetradecan-9-one.

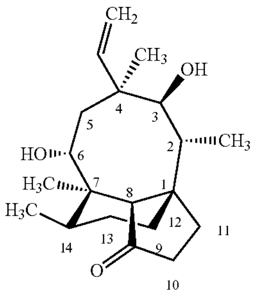 [SMILES: C=C[C@]1(C)C[C@@H](O)[C@]2(C)C(C)CC[C@]3(CCC(=O)[C@H]32)[C@@H](C)[C@@H]1O]

In the following examples, pleuromutilin derivatives are numbered in analogy to the mutilin numbering system described by H. Berner (Berner, H.; Schulz, G.; Schneider H. *Tetrahedron* 1980, 36, 1807-1811):

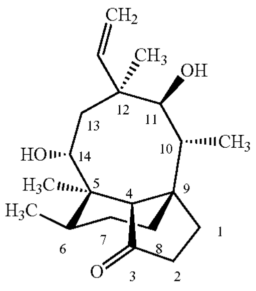 [SMILES: C=C[C@]1(C)C[C@@H](O)[C@]2(C)C(C)CC[C@]3(CCC(=O)[C@H]32)[C@@H](C)[C@@H]1O]

In the compounds of the present invention, e.g. in the compounds of example 1, the stereochemistry of the methyl group at position 12 (and in turn also the stereochemistry of the second group attached in position 12 of the mutilin ring) is inverted (epi-mutilin derivatives) and in addition the vinyl group is altered and various substituents instead of vinyl have been introduced:

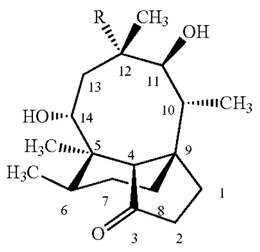

12-Epi-pleuromutilin and 12-epi-pleuromutilin tosylate are compounds of formulae:

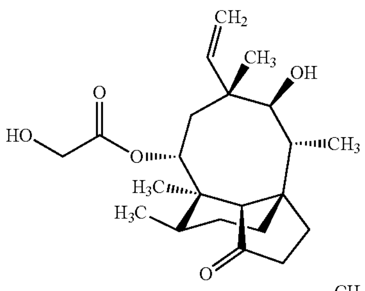

or

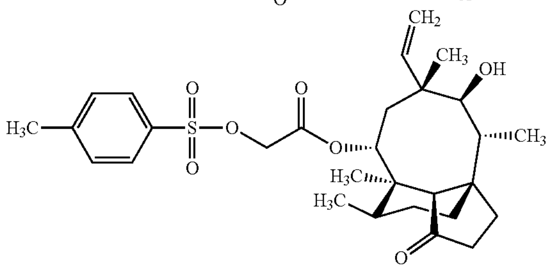

respectively.

Herein, including the examples and the reaction scheme the following abbreviations are used:

1H-NMR proton nuclear magnetic resonance spectroscopy

° C. degrees Celsius

μM micromolar concentration

BC 9842 12-epi-12-desvinyl-14-O-[(Piperidin-4-ylsulfanyl]-acetyl]-12-[2-(3-methyl-pyrazin-2-yl)-ethenyl]-mutilin BOC tert-butyloxycarbony CoV corona virus CPE cytopathic effects, in particular virus-induced DMEM Dulbecco's modified Eagle's medium EC50 Half maximal (fifty-percent) effective concentration EtOAc ethyl acetate FBS Fetal bovine serum HeLa immortal human epithelial cell line HEp2 human epithelial cell line M molarity m/z mass/charge ratio
MOI Multiplicity of infection
MRC-5 Medical Research Council cell strain 5
MS mass spectrometry
nm nanometer
TC50 Half maximal (fifty-percent) toxic concentration
TCID50 Fifty-percent (half maximal) tissue culture infective dose
XTT 2,3-bis-(2-methoxy-4-nitro-5-sulfophenyl)-2H-tetrazolium-5-carboxanilide Example 1: Preparation of BC 9842

12-epi-12-Desvinyl-14-O-[(Piperidin-4-ylsulfanyl)-acetyl]-12-[(E)-2-(3-methyl-pyrazin-2-yl)-vinyl]-mutilin dihydrochloride Step 1: 12-epi-14-O-[(1-tert-Butoxycarbonyl-piperidine-4-ylsulfanyl)-acetyl]-mutilin To 12-epi-Pleuromutilintosylate (37.2 g) was added methanol (200 mL), tert-butyl 4-acetylsulfanylpiperidine-1-carboxylate (18.1 g) as well as potassium carbonate solution (5M in water, 55.9 mL) and sonicated for 1.5 hours in an ultrasonic bath at room temperature. The resulting solution was concentrated to dryness, taken up in ethyl acetate and washed twice with half-saturated NaCl solution. The organic phase was dried over anhydrous Na2SO4 and evaporated to dryness under reduced pressure to obtain the title compound (quantitative yield containing residual solvent) in the form of a pale-yellow to yellow solid. The crude product is used for the next step without further purification.

1H-NMR (400 MHz, CDCl3, δ, ppm, characteristic signals, mutilin numbering system): 5.74-5.62 (m, 1H, H-19), 5.56 (d, 1H, H-14, J=8.0 Hz), 5.20-5.07 (m, 2H, H-20), 4.01-3.80 (m, 2H, H-22), 3.37 (d, 1H, H-11, J=6.0 Hz), 1.39 (m, 12H, BOC, CH3-15), 1.15 (s, 3H, CH3-18), 0.89 (d, 3H, CH3-17, J=6.8 Hz), 0.66 (d, 3H, CH3-16, J=6.8 Hz).

MS m/z: 612 [M+Cl−], 622 [M+HCOO−].

Step 2: 12-epi-12-desvinyl-14-O-[(1-tert-Butoxycarbonyl-piperidin-4-ylsulfanyl)-acetyl]-12-[2-(3-methyl-pyrazin-2-yl)-ethenyl]-mutilin 2-Bromo-3-methylpyrazine (95%, 5.99 g) and bis-(benzonitrile)-palladium(II)-chlorid (2.66 g) were suspended in ethylene glycol (400 mL). Then 12-epi-14-O-[(1-tert-Butoxycarbonyl-piperidine-4-ylsulfanyl)-acetyl]-mutilin (10 g), N-methyl-morpholine (15.22 mL) and ethylene glycol (600 mL) were added subsequently to give an orange suspension. The resulting mixture was stirred at 110° C. overnight. The reaction mixture was diluted with ethyl acetate, extracted with 0.05M HCl/NaCl solution (500 mL, 0.1 M aqueous HCl+5% aqueous NaCl solution, 1:1) and twice with 5% aqueous NaCl solution. The aqueous phases were washed with ethyl acetate. All organic phases were combined, washed with saturated aqueous NaCl solution, dried over anhydrous Na2SO4 and concentrated under reduced pressure. The evaporation residue was subjected to chromatography over silica gel using cyclohexane/EtOAc 1:10 and EtOAc as eluents to obtain the title compound (1.39 g) as a pale-yellow to yellow solid.

1H-NMR (400 MHz, CDCl3, δ, ppm, characteristic signals, mutilin numbering system): 8.29-8.23 (m, 2H, aromat.), 6.86 and 6.64 (2d, 2H, H-19, H-20, J=15.4 Hz), 5.59 (d, 1H, H-14, J=8.4 Hz), 4.00-3.80 (m, 2H, H-22), 3.60 (d, 1H, H-11, J=6.4 Hz), 2.55 (s, 3H, CH3-aromat.), 1.42-1.32 (m, 15H, BOC, CH3-15, CH3-18), 0.91 (d, 3H, CH3-17, J=6.8 Hz), 0.68 (d, 3H, CH3-16, J=6.8 Hz).

MS m/z: 670 [M+H+], 714 [M+HCOO−].

Step 3: 12-epi-12-desvinyl-14-O-[(Piperidin-4-ylsulfanyl]-acetyl]-12-[2-(3-methyl-pyrazin-2-yl)-ethenyl]-mutilin dihydrochloride 12-epi-12-desvinyl-14-O-[(1-tert-Butoxycarbonyl-piperidin-4-ylsulfanyl)-acetyl]-12-[2-(3-methyl-pyrazin-2-yl)-ethenyl]-mutilin (1.39 g) was dissolved in dichloromethane and trifluoroacetic acid (10 mL) was added. The reaction mixture was stirred for 30 minutes at room temperature and evaporated to dryness. The resulting residual was dissolved in dichloromethane and hydrogen chlorid (2M in diethylether, 10 mL) was added. The resulting mixture was evaporated again to dryness and the resulting residual was dissolved in water, washed three times with diethylether and lyophilized to obtain the title compound (925 mg) as an orange solid.

1H-NMR (400 MHz, DMSO-d6, δ, ppm, characteristic signals, mutilin numbering system): 9.40-9.05 (m, 2H, NH2), 8.50-8.32 (m, 2H, aromat.), 7.15 and 6.53 (2d, 2H, H-19, H-20, J=16 Hz), 5.57 (d, 1H, H-14, J=7.6 Hz), 3.76-3.67 (m, 1H, H-11), 2.57 (s, 3H, CH3-aromat.), 1.40 (s, 3H, H-15), 1.23 (s, 3H, H-18), 0.88 (d, 3H, H-17, J=6.4 Hz), 0.67 (d, 3H, H-16, J=6.0 Hz).

MS m/z: 570 [M+H+], 604 [M+Cl−].

Example 2: Anti-Coronavirus Cytoprotection Assay

Objective: The assay measured the inhibition of virus-induced cytopathic effects (CPE) and cell viability following alpha coronavirus 229E (HCoV-229E or CoV229E) in MRC-5 cells 6 days post infections with the virus by various concentrations of the investigated compounds.

Methodology: MRC-5 cells were seeded in 96-well flat-bottom tissue culture plates (at a density of 3×103 cells per well) and allowed to adhere overnight. Thereafter, diluted test compounds (BC-9842 as dihydrochloride, Tiamulin as fumarate) in DMSO were added to the plate and incubated for 4 hours prior to addition of the virus. The virus was added diluted to a pre-determined titer to yield 85-95% cell killing at 6 days post-infection (MOI of 0.001).

Following incubation at 37° C. and at 5% CO2 for 6 days, cell viability was measured by XTT tetrazolium dye staining. The optical density of the cell culture plate was determined spectrophotometrically at 450 and 650 nm. Percent reduction of the virus-infected cells and the percent cell viability of uninfected drug control wells were calculated to determine the effective concentration at which 50% of cytopathic effect was inhibited ($EC_{50}$) and the cytotoxic concentration ($TC_{50}$) using four parameter curve fit analysis. The antiviral compound Remdesivir served as positive control.

Results:

Surprisingly, BC 9842 reduced the viral CPE by 100% at concentrations of 5 μM and 10 μM, which are concentrations that had no cytotoxic effect on the viability of the cell control. The calculated $EC_{50}$ was 1.92 μM, at which 50% of the viral cytopathic effect was inhibited. At the BC 9842 concentration of 50 μM, BC 9842 displayed a cytotoxic effect; the calculated $TC_{50}$ was 22.4 μM. The ratio of $EC_{50}$ and $TC_{50}$, known also as therapeutic index, was 11.7.

In contrast, Tiamulin at a concentration of 10 μM reduced the viral CPE only by 10.53% and no cytotoxic effect was observed. At the next higher test concentration of 50 μM the CPE was reduced by 81.68% and a cytotoxic effect was observed. The calculated $EC_{50}$ was 24.4 μM and the calculated $TC_{50}$ was 62.9 μM. The therapeutic index of Tiamulin was 2.58 and surprisingly much lower than that of BC 9842.

The antiviral compound Remdesivir was developed as a treatment for Ebola virus, and also is known to have antiviral activity against corona viruses (clinical investigation is ongoing). Thus, Remdesivir served as positive control herein. Remdesivir showed an $EC_{50}$ of 0.11 μM, a $TC_{50}$ of >5 and a therapeutic index of >45.5.

| | MRC-5 cells infected with human corona virus (CoV229E) | | |
|---|---|---|---|
| Compound | $EC_{50}$ (μM) | $TC_{50}$ (μM) | Therapeutic Index |
| BC 9842 | 1.92 | 22.4 | 11.7 |
| Tiamulin | 24.4 | 62.9 | 2.58 |
| Remdesivir | 0.11 | >5.00 | >45.5 |

The results are graphically displayed in FIGS. 1 (BC 9842), 2 (Tiamulin) and 3 (Remdesivir) (VC . . . reduction of viral CPE, CC . . . Cell Control).

Example 3: Anti-Respiratory Syncytial Virus (RSV) Cytoprotection Assay

Objective: The assay measured the inhibition of virus-induced cytopathic effects (CPE) and cell viability following human respiratory syncytial virus (strain RSVA2) replication in HEp2 cells 6 days post infections with the virus by various concentrations of BC 9842.

Methodology: HEp2 cells were seeded in 96-well flat-bottom tissue culture plates (at a density of 5×103 cells per well) and allowed to adhere overnight. Thereafter, diluted test compounds (BC 9842 as dihydrochloride, Tiamulin as fumarate) in DMSO were added to the plate and incubated for 4 hours prior to addition of the virus. The virus was added diluted to a pre-determined titer to yield 85-95% cell killing at 6 days post-infection (MOI of 0.001).

Following incubation at 37° C. and at 5% $CO_2$ for 6 days, cell viability was measured by XTT tetrazolium dye staining. The optical density of the cell culture plate was determined spectrophotometrically at 450 and 650 nm. Percent reduction of the virus-infected cells and the percent cell viability of uninfected drug control wells were calculated to determine the effective concentration at which 50% of cytopathic effect was inhibited ($EC_{50}$) and the cytotoxic concentration ($TC_{50}$) using four parameter curve fit analysis. The antiviral compound TMC353121 (RSV fusion inhibitor) served as positive control.

Results:

Surprisingly, BC 9842 reduced the viral cytopathic effect (CPE) by 52.85% and 69.33% at concentrations of 5 μM and 10 μM, respectively, which are concentrations that had no cytotoxic effect on the viability of the cell control. The calculated $EC_{50}$ was 4.58 μM, at which 50% of the viral CPE was inhibited. At the BC 9842 concentration of 50 μM, BC 9842 displayed a cytotoxic effect; the calculated $TC_{50}$ was 22.4 μM. The ratio of $EC_{50}$ and TCso, known also as therapeutic index, was 4.89.

In contrast, Tiamulin at a concentration of 10 μM reduced the viral CPE only by only 16.76% and a cytotoxic effect (84% viability) was observed at this concentration. At the next higher test concentration of 50 μM the viral CPE was reduced by 43.28% and at the cytotoxic effect was more pronounced (70.0% viability). The calculated $EC_{50}$ was with >67.9 μM above the calculated $TC_{50}$ of 67.9 μM. The therapeutic index of Tiamulin therefore could not be calculated. Surprisingly, the antiviral activity and therapeutic index was much higher for BC-9842 than for Tiamulin.

The antiviral compound TMC353121 was developed as a specific respiratory syncytial virus fusion inhibitor (clinical investigation is ongoing). Thus, TMC353121 served as positive control herein. TMC353121 showed an $EC_{50}$ of 0.006 μM, a $TC_{50}$ of >0.1 μM and a therapeutic index of >167.

| | HEp2 cells infected with human respiratory syncytial virus (RSVA2) | | |
|---|---|---|---|
| Compound | $EC_{50}$ (μM) | $TC_{50}$ (μM) | Therapeutic Index |
| BC-9842 | 4.58 | 22.4 | 4.89 |
| Tiamulin | >67.9 | 67.9 | — |
| TMC353121 | 0.0006 | >0.1 | >167 |

Figure 4:
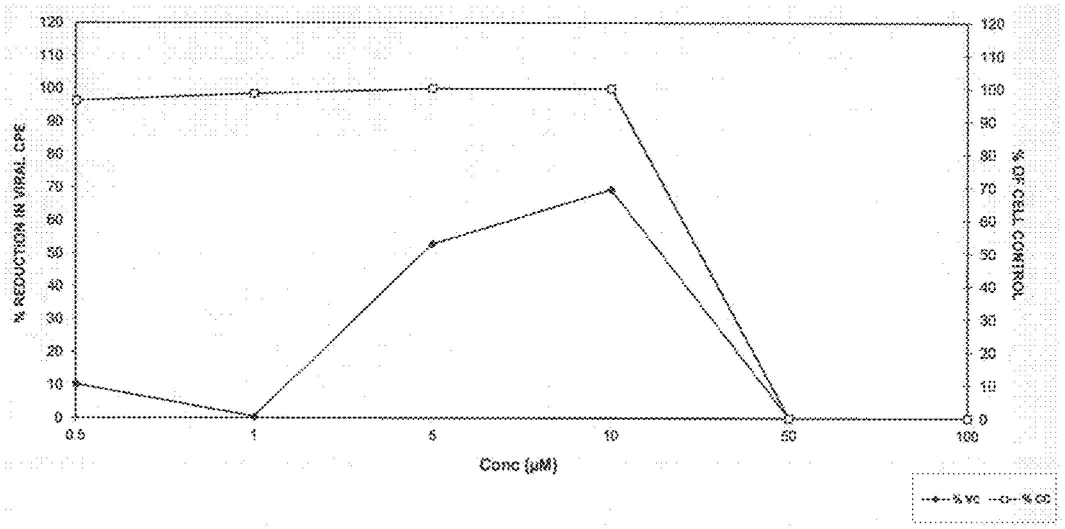
FIG. 4 demonstrates the effect of the compound of claim 16 (BC 9842) against respiratory syncytial virus type A in HEp2 cells 6 days post infections with the virus.
Figure 5:
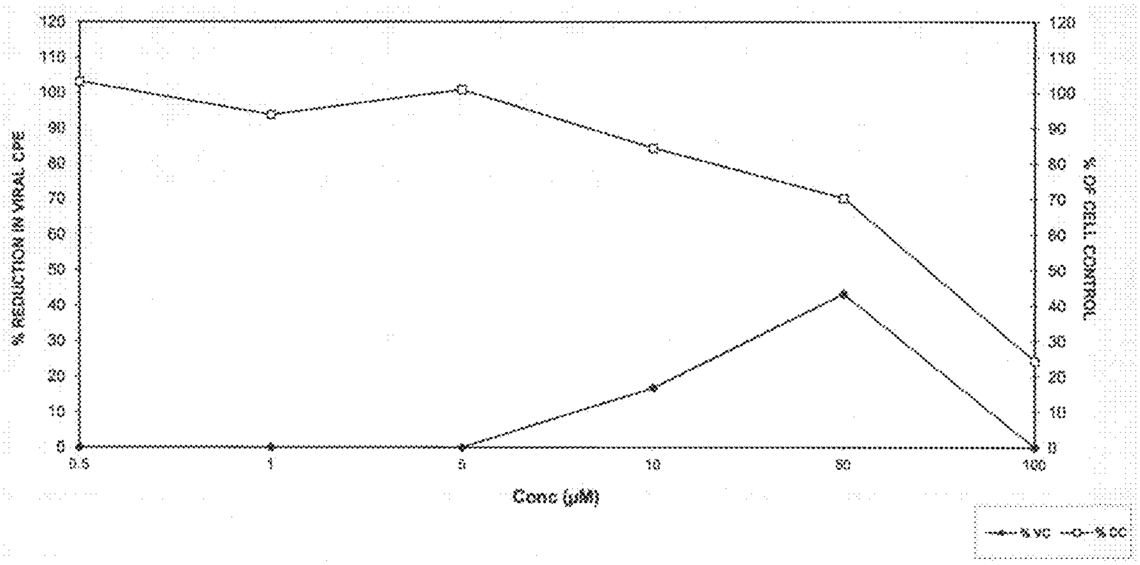
FIG. 5 demonstrates the effect of Tiamulin in the same assay.
Figure 6:
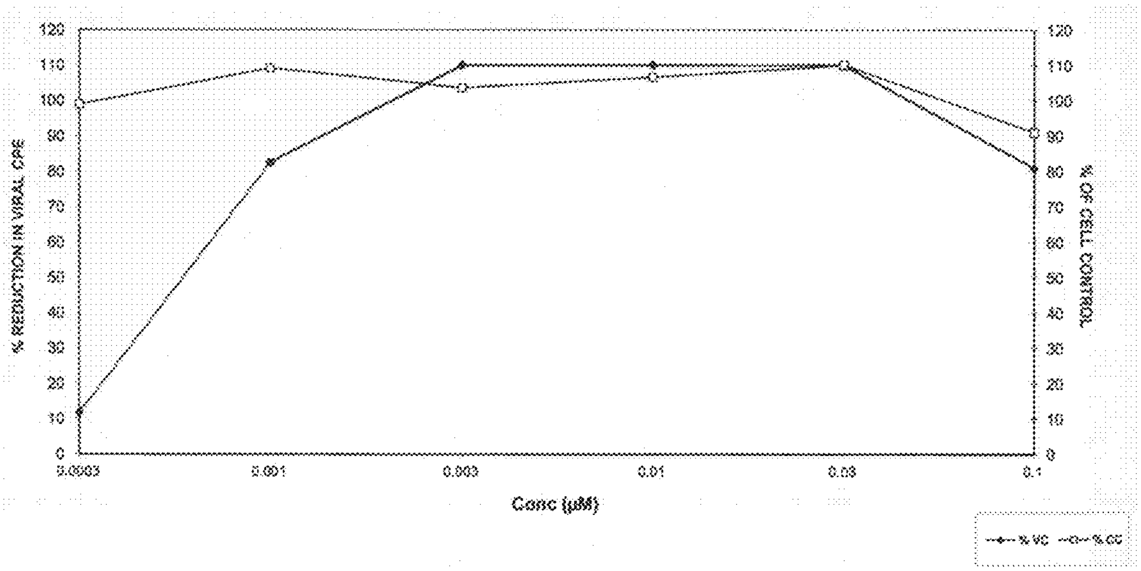
FIG. 6 demonstrates the effect of TMC353121 in the same assay.

The results are graphically displayed in FIGS. 4 (BC 9842), 5 (Tiamulin) and 6 (TMC353121) (VC . . . reduction of viral CPE, CC . . . Cell Control).

Example 4: Anti-Respiratory Syncytial Virus (RSV) Cytoprotection Assay Using Different RSV Strains Objective: The assay measured the inhibition of virus-induced cytopathic effects (CPE) and cell viability following replication of the two different respiratory syncytial virus strains RSV ALONG and RSV B18537 in HEp2 cells.

Methodology: The assay was performed in analogy to Example 3 above with the difference that cells seeded with a density of 5×103 cells per well were incubated with the virus strains RSV ALONG or RSV B18537, respectively, following a 4 hour cell pretreatment with the test compound at different concentrations. Virus was diluted and added in an amount yielding an MOI of 0.01 and 0.001 for RSV ALONG and RSV B18537, respectively.

Results:

The antiviral efficacy and cellular toxicity data are summarized in the tables below. The control compound TMC353121 was evaluated in parallel to BC-9842 and yielded an $EC_{50}$ value of 0.01 nM against the investigated strains of RSV A and RSV B. BC 9842 yielded an $EC_{50}$ values of 6.77 μM against the RSV B18537. Activity against RSV ALONG could not be determined due to the cytotoxicity to HEp2 cells with $TC_{50}$ values of 22.4 μM in the assay.

| | HEp2 cells infected with respiratory syncytial virus (RSV ALONG) | | |
|---|---|---|---|
| Compound | $EC_{50}$ (μM) | $TC_{50}$ (μM) | Therapeutic Index |
| BC 9842 | >22.4 | 22.4 | — |
| TMC353121 | 0.00001 | >1.00 | >100000 |

| | HEp2 cells infected with respiratory syncytial virus (RSV B18537) | | |
|---|---|---|---|
| Compound | $EC_{50}$ (μM) | $TC_{50}$ (μM) | Therapeutic Index |
| BC 9842 | 6.77 | 22.4 | 3.31 |
| TMC353121 | 0.00001 | >1.00 | >100000 |

Example 5: Anti-Measles Virus (RSV) Cytoprotection Assay

Objective: The assay measured the inhibition of virus-induced cytopathic effects (CPE) and cell viability during replication of Measles virus strain Edmonston in HeLa cells.

Method: HeLa cells were seeded in 96-well flat-bottom tissue culture plates (at a density of 5×103 cells per well) and allowed to adhere overnight. Thereafter, diluted test compounds (BC 9842 as dihydrochloride, Ribavirin for control) were added to the plate and incubated for 4 hours prior to addition of the virus. Virus was added diluted to a predetermined titer to yield 85-95% cell killing at 6 days post-infection (1:50 dilution, MOI of 0.008).

Cell viability determination and calculation of $EC_{50}$ and $TC_{50}$ were performed as described in Examples 2 and 3.

Results:

The antiviral efficacy and cellular toxicity data are summarized in the Table below. Ribavirin was evaluated as control compound in parallel to BC 9842 and yielded an $EC_{50}$ value of 1.88 μg/mL. BC 9842 reduced the viral CPE by 69% at a concentration of 10 μM and an $EC_{50}$ value of 5.36 μM was calculated.

| | HeLa Cells infected with Measles virus (strain Edmonston) | | |
|---|---|---|---|
| Compound | $EC_{50}$ (μM) | $TC_{50}$ (μM) | Therapeutic Index |
| BC 9842 | 5.36 | 24.1 | 4.5 |
| Ribavirin (μg/mL) | 1.88 | 21.6 | 11.5 |

Example 6: Antibacterial Activity of BC-9842

The in vitro activity against bacteria including isolates that are resistant to Lefamulin was determined by standard broth microdilution according to the Clinical and Laboratory Standards Institute CLSI document (Performance Standards for Antimicrobial Susceptibility Testing) M100Ed29E (2019) and (Methods for Dilution Antimicrobial Susceptibility Test for Bacteria That Grow Aerobically) M07Ed11 (2018) or other years' versions thereof. The data were obtained using cation-adjusted Mueller Hinton broth medium (CAMHB).

Results for BC-9842 in comparison to Example 154 of WO 2015/110481 A1 (12-epi-12-desvinyl-14-O-[(azepan-4-ylsulfanyl)-acetyl]-12-((E)-2-pyridin-3-yl-ethenyl) mutilin hydrochloride) and Lefamulin are summarized in the table below.

| MIC [μg/mL] | BC-9842 | Example 154 of WO 2015/110481 | Lefamulin |
|---|---|---|---|
| *Staphylococcus aureus* ATCC49951 | ≤0.03 | ≤0.03 | ≤0.03 |
| *Staphylococcus aureus* cfr (+) (n = 2) | 1-2 | 0.5-4 | 16 |
| *Staphylococcus aureus* vga(A) (+) | 4 | 2-4 | 8 |
| *Streptococcus pneumoniae* ATCC49619 | ≤0.03 | ≤0.03 | ≤0.03 |
| *Streptococcus agalactiae* lsa(E) (n = 2) | 0.5-1 | 4-8 | 16 |

BC-9842 exhibits MICs≤0.1 μg/ml against *Staphylococcus aureus* ATCC49951, and *Streptococcus pneumoniae* ATCC49619. In addition, BC-9842 exhibits MICs≤4 μg/ml against Lefamulin resistant *Staphylococcus aureus* strains mediated by e.g. cfr or vga(A) and Lefamulin resistant *Streptococcus agalactiae* strains mediated by e.g. lsa(E) resistance mechanisms.

Example 7: Metabolic Stability of BC-9842

The metabolic stability of BC-9842 was determined by using cryopreserved primary mouse or human hepatocytes. About 1.00×105 cells/mL in Krebs-Henseleit buffer (KIHB) were incubated in the absence and the presence of 1 μg/mL of the test compounds at 37° C., 500 $CO_2$ for 4 hours (in triplicate). Test compounds were dissolved in dimethyl sulfoxide (DMSO) and further diluted with KHIB, so that the DMSO concentration in the assay was ≤0.200. To evaluate the non-enzymatic degradation under assay conditions, a sample of each test compound was incubated also in the absence of hepatocytes. Samples were taken immediately and after 4 hours of incubation with test compounds. The incubation was stopped by adding the same volume of acetonitrile, vortexing and, freezing the reaction mixture. After thawing, vortexing, and centrifugation, the centrifugate was diluted with acidified (100 formic acid) water and analyzed for parent compound disappearance or metabolite appearance using LC/MS. The metabolic stability value corresponds to the remaining parent compound in % after 4 hours of incubation.

Results for BC-¬9842 in comparison to Example 154 from WO 2015/110481 A1 (12-epi-12-desvinyl-14-O-[(azepan-4-ylsulfanyl)-acetyl]-12-((E)-2-pyridin-3-yl-ethenyl) mutilin hydrochloride) are summarized below.

| Metabolic stability against primary hepatocytes [% parent compound] | BC-¬9842 | Example 154 from WO 2015/110481 |
|---|---|---|
| mouse | 63.8% | 0% |
| human | 24.7% | 0% |

BC-9842 displays a metabolic stability of >60% after incubation with primary mouse hepatocytes and >20% after incubation with primary human hepatocytes. Especially in comparison to the low metabolic stability of Example 154 from WO 2015/110481, this represents a valid improvement towards its usability as drug substance.

The invention claimed is:

1. A compound of formula (II)

(II)

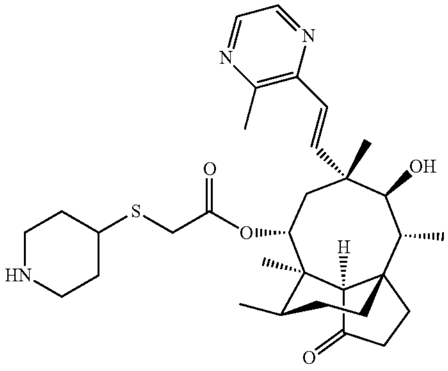

or a pharmaceutically acceptable salt or solvate thereof.

2. A pharmaceutical composition comprising a compound of claim 1 or the pharmaceutically acceptable salt or solvate thereof, with at least one pharmaceutical excipient, optionally further comprising another pharmaceutically active agent.

3. A method of treating or preventing a viral infection comprising administering to a subject in need thereof a compound of claim 1 or the pharmaceutically acceptable salt or solvate thereof.

4. The method according to claim 3, wherein the viral infection relates to a respiratory disease.

5. The method according to claim 3, wherein the viral infection relates to an acute respiratory syndrome optionally including Influenza, Severe Acute Respiratory Syndrome (SARS), Middle East Respiratory Syndrome (MERS) or COVID-19.

6. The method according to claim 3, wherein the viral infection is associated with a virus being a positive- or negative-sense single-stranded RNA virus, optionally the virus is Coronaviridae, optionally including human coronavirus,
Paramyxoviridae, optionally including Paramyxovirinae, optionally including Measles virus, or Pneumovirinae, optionally including Respiratory Syncytial Virus,
Orthomyxoviridae, optionally including Influenza virus,
Flaviviridae, optionally including Dengue virus or Zika virus, or
Picornaviridae, optionally including Rhinovirus.

7. The method according to claim 3, wherein the viral infection relates to an airborne disease.

8. A method for treating or preventing a viral infection, comprising administering to a subject in need thereof a compound of formula (I)

(I)

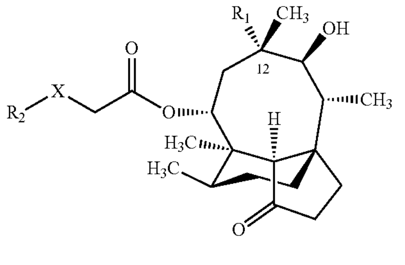

, wherein $R_1$ is ($C_{1-16}$)alkyl or ($C_{2-16}$)alkenyl substituted by heterocyclyl including aliphatic and aromatic heterocyclyl and comprising 1 to 4 heteroatoms selected from N, O, and S, provided that at least one heteroatom is a nitrogen atom, or $R_1$ is

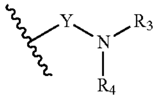

wherein Y—N($R_3R_4$) is
($C_{1-16}$)alkyl-N($R_3R_4$),
($C_{1-16}$)alkyl-($C_{6-14}$)aryl-N($R_3R_4$),
($C_{1-16}$)alkyl-($C_{6-14}$)aryl-($C_{1-16}$)alkyl-N($R_3R_4$),
($C_{1-16}$)alkyl-($C_{1-13}$)heterocyclyl-N($R_3R_4$),
($C_{1-16}$)alkyl-($C_{1-13}$)heterocyclyl-($C_{1-16}$)alkyl-N($R_3R_4$),
carbonyl-N($R_3R_4$),
($C_{1-4}$)alkyl-carbonyl-N($R_3R_4$),
($C_{2-16}$)alkenyl-N($R_3R_4$),
($C_{2-16}$)alkenyl-($C_{6-14}$)aryl-N($R_3R_4$),
($C_{2-16}$)alkenyl-($C_{6-14}$)aryl-($C_{1-16}$)alkyl-N($R_3R_4$),
($C_{2-16}$)alkenyl-($C_{1-13}$)heterocyclyl-N($R_3R_4$), or
($C_{2-16}$)alkenyl-($C_{1-13}$)heterocyclyl-($C_{1-16}$)alkyl-N ($R_3R_4$),
wherein heterocyclyl includes aliphatic and aromatic heterocyclyl and comprises at least one heteroatom selected from N, O, and S, and
wherein alkyl, aryl, heterocyclyl, or alkenyl is optionally substituted by one or more substituents optionally having one or more heteroatoms selected from O, N, S, and halogen;
wherein each of $R_3$ and $R_4$ is independently
hydrogen,
($C_{1-16}$)alkyl,
($C_{2-16}$)alkenyl,
hydroxy-($C_{1-16}$)alkyl,
amino-($C_{1-16}$)alkyl,
mono- or di-($C_{1-6}$)alkylamino($C_{1-16}$)alkyl,
guanidino ($C_{1-16}$)alkyl, ureido ($C_{1-16}$)alkyl, or thioureido ($C_1$-16)alkyl,
amino ($C_{1-6}$)alkyl-($C_{6-14}$)aryl-($C_{1-6}$)alkyl,
amino($C_{1-6}$)alkyl-($C_{6-14}$)aryl,
guanidino ($C_{1-6}$)alkyl-($C_{6-14}$)aryl-($C_{1-6}$)alkyl,
amino($C_{1-6}$)alkyloxy-($C_{1-6}$)alkyl,
amino($C_{3-8}$) cycloalkyl,
amino($C_{1-6}$)alkyl-($C_{3-8}$) cycloalkyl,
amino($C_{3-8}$) cycloalkyl-($C_{1-6}$)alkyl,
amino($C_{1-6}$)alkyl-($C_{3-8}$) cycloalkyl-($C_{1-6}$)alkyl,
($C_{1-13}$)heterocyclyl-($C_{1-16}$)alkyl,
($C_{6-14}$)aryl-($C_{1-16}$)alkyl,
($C_{1-13}$)heterocyclyl,
amino($C_{6-14}$)aryl-($C_{1-16}$)alkyl,
amino($C_{1-6}$)alkyloxy-($C_{6-14}$)aryl-($C_{1-6}$)alkyl,
amino($C_{1-6}$)alkyl-($C_{6-12}$)aryl-carbonyl,
amino($C_{1-6}$)alkyl-amido-($C_{6-12}$)aryl($C_{1-6}$)alkyl,
($C_{1-4}$)alkylcarbonyl, or
carbamimidoyl, carbamoyl, or thiocarbamoyl,
wherein heterocyclyl includes aliphatic and aromatic heterocyclyl and comprises at least one heteroatom selected from N, O, and S, and
wherein alkyl, cycloalkyl, heterocyclyl, alkenyl, or aryl is optionally substituted by
amino($C_{1-4}$)alkyl, amido, mono- or di-($C_{1-4}$)alkylamido, ($C_{1-6}$)alkyloxy-carbonyl, halogen, oxo, or hydroxy, wherein X is sulfur or oxygen, and wherein $R_2$ is a hydrocarbon group comprising 1 to 22 carbon atoms, optionally comprising heteroatoms selected from N, O, S, and halogen, or a pharmaceutically acceptable salt or solvate, thereof.

9. The method according to claim 8, wherein, in the compound or the pharmaceutically acceptable salt or solvate, thereof, $R_2$ is $(C_{1-16})$alkyl, $(C_{3-12})$ cycloalkyl, $(C_{1-13})$heterocyclyl, or $(C_{6-14})$aryl, wherein heterocyclyl includes aliphatic and aromatic heterocyclyl and comprises at least one heteroatom selected from N, O, and S, and wherein alkyl, cycloalkyl, aryl, heterocyclyl is optionally substituted by one or more substituents having one or more heteroatoms selected from O, N, S, and halogen.

10. The method according to claim 9, wherein, in the compound or the pharmaceutically acceptable salt or solvate thereof, $R_2$ is $(C_{1-16})$alkyl, optionally substituted by hydroxy or amino, $(C_{3-12})$ cycloalkyl optionally substituted by amino or amino$(C_{1-4})$alkyl, the amino or amino$(C_{1-4})$alkyl optionally further substituted by amino$(C_{1-6})$alkylcarbonyl or $(C_{1-4})$alkyl, $(C_{2-11})$heterocyclyl having at least one nitrogen heteroatom and being optionally further substituted by amino$(C_{1-6})$alkylcarbonyl;

$R_2$ is cycloalkyl, optionally substituted by amino$(C_{1-4})$alkyl, wherein amino is optionally further substituted by amino$(C_{1-6})$alkylcarbonyl, hydroxy, amino optionally substituted by amino$(C_{1-6})$alkylcarbonyl or $(C_{1-4})$alkyl, amino and hydroxy, wherein amino is optionally further substituted by amino$(C_{1-6})$alkylcarbonyl or $(C_{1-4})$alkyl, $(C_{1-4})$alkylamino optionally further substituted by one or more halogen atoms;

$R_2$ is aliphatic $(C_{2-11})$heterocyclyl comprising 1 to 4 heteroatoms selected from N, O, and S, wherein a nitrogen heteroatom is optionally substituted by $(C_{1-4})$alkyl, or amino$(C_{1-6})$alkylcarbonyl;

$R_2$ is aryl optionally substituted by hydroxy, halogen, amino, hydroxy $(C_{1-4})$alkyl, bis-(hydroxy $(C_{1-4})$alkyl), amino$(C_{1-4})$alkyl, bis-(amino $(C_{1-4})$alkyl), wherein amino in amino$(C_{1-4})$alkyl is optionally further substituted, $(C_{1-6})$alkyl optionally substituted by aminocarbonyl, wherein the nitrogen of the aminocarbonyl group is optionally further substituted by amino$(C_{1-12})$alkyl, diamino-$(C_{1-12})$alkyl, bis-(amino$(C_{1-12})$alkyl), hydroxy $(C_{1-6})$alkyl, bis-(hydroxy $(C_{1-6})$alkyl), acylated amino$(C_{1-4})$alkyl, aminocarbonyl, wherein nitrogen is optionally further substituted by amino$(C_{1-12})$alkyl, bis-(amino$(C_{1-12})$alkyl), hydroxy $(C_{1-6})$alkyl, bis-(hydroxy $(C_{1-6})$alkyl), diamino$(C_{1-6})$alkyl, or $(C_{1-12})$alkyl, optionally further substituted by amino, optionally further substituted by formyl, $(C_{1-4})$alkylcarbonyl, a 4- to 8-membered saturated or unsaturated heterocyclyl comprising 1 to 3 heteroatoms selected from N, O, and S, or $(C_{6-14})$aryl optionally further substituted by amino$(C_{1-4})$alkyl or wherein nitrogen is part of $(C_{3-8})$heterocyclyl, including aliphatic and aromatic heterocyclyl, comprising one or more heteroatoms selected from N, O, S and being optionally further substituted by amino $(C_{1-4})$alkyl; or $R_2$ is aromatic $(C_{1-13})$heterocyclyl comprising 1 to 4 heteroatoms and being optionally substituted by $(C_{1-6})$ alkyl, amino, or hydroxy, wherein alkyl is optionally further substituted by halogen or amino, or being optionally substituted by aminocarbonyl, wherein amino is optionally further substituted by amino $(C_{1-12})$alkyl, bis-(amino$(C_1$-12)alkyl), hydroxy $(C_{1-6})$alkyl, bis-(hydroxy $(C_{1-6})$alkyl), or diamino$(C_{1-6})$alkyl.

11. The method according to claim 8, wherein, in the compound or the pharmaceutically acceptable salt or solvate thereof, $R_2$ is amido-phenyl, amido $(C_{1-4})$alkyl-phenyl, wherein nitrogen of amido is optionally substituted by amino$(C_{1-8})$alkyl, wherein alkyl is optionally further substituted.

12. The method according to claim 8, wherein, in the compound or the pharmaceutically acceptable salt or solvate thereof, $R_2$ is amino$(C_{3-12})$ cycloalkyl, amino$(C_{1-4})$alkyl$(C_{3-12})$ cycloalkyl, amino$(C_{3-12})$ cycloalkyl$(C_{1-4})$alkyl, or amino$(C_{1-4})$alkyl$(C_{3-12})$ cycloalkyl$(C_{1-4})$alkyl, wherein amino is optionally substituted by amino$(C_{1-6})$ alkylcarbonyl or $(C_{1-4})$alkyl.

13. The method according to claim 8, wherein, in the compound or the pharmaceutically acceptable salt or solvate thereof, $R_2$ is $(C_{2-11})$heterocyclyl comprising 1 to 4 heteroatoms selected from N, O, S, wherein, if $R_2$ has at least one nitrogen heteroatom, the at least one nitrogen heteroatom is optionally substituted by $(C_{1-4})$alkyl, or amino$(C_{1-6})$alkylcarbonyl.

14. The method according to claim 8, wherein, in the compound or the pharmaceutically acceptable salt or solvate thereof, X is S, and $R_2$ is aminoethyl-amidomethyl-phenyl, aminopropyl-amidomethyl-phenyl, hydroxyphenyl-(amino)ethyl-amidomethyl-phenyl, aminomethyl-phenyl-(amino)ethyl-amidomethyl-phenyl, aminopropyl-amidophenyl, aminomethyl-phenylmethyl-amido-phenyl, aminomethyl-phenyl, aminoacetyl-aminomethyl-phenyl, bis(aminomethyl)phenyl, bisaminopropyl-amidomethyl-phenyl, (2-amino)-aminopropyl-amidomethyl-phenyl, aminoethyl-aminomethyl-phenyl, aminopropyl-aminomethyl-phenyl, allyl-aminomethyl-phenyl, aminomethyl-phenylmethyl-aminomethyl-phenyl, hydroxymethyl-phenyl, bis(hydroxymethyl)-phenyl, (tetrafluoro-hydroxymethyl)-phenyl, amino-hydroxy-cyclohexyl, hydroxyethyl, aminoethyl, piperazinocarbonyl-phenyl, aminomethyl-piperidine-carbonyl-phenyl, piperidine-ylmethyl-amido-phenyl, pyridine-ylmethyl-amido-phenyl, acetyl-aminopropyl-amido-phenyl, formyl-aminopropyl-amido-phenyl, amido-phenyl, aminohexyl-amidophenyl, aminoethyl-amidophenyl, (5-Amino)-4H-[1,2,4]triazol-3-yl, pyridinyl, hydroxyphenyl, fluorophenyl, purinyl, aminophenyl, acetyl-aminomethyl-phenyl, cyclopropyl-aminomethyl-phenyl, aminopropyl-amidopyridinyl, hydroxypropyl-amidophenyl, amino-purinyl, difluoroethylamino-cyclohexyl, amino-hydroxy-cyclohexyl, azepanyl, aminomethyl-cyclohexylmethyl, N-methyl-piperidinyl, piperidinyl, aminomethylcyclohexyl, aminopropylphenyl, phenyl, N-aminomethylcarbonyl-piperidinyl, N-aminoethylcarbonyl-piperidinyl, N-aminomethyl-carbonyl-piperidinylmethyl, aminomethylamidomethylcyclohexyl, aminomethyl-pyridinyl, or aminomethylamidocyclohexyl.

15. The method according to claim 8, wherein the compound is of formula (III)

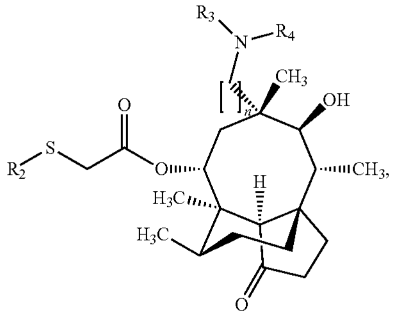

(III)

wherein n is 1 to 12, $R_3$ is H, aminoethyl, aminopropyl, aminobutyl, aminopentyl, aminohexyl, aminooctyl, aminodecyl, dimethylaminopropyl, dimethylamidopentyl, guanidinobutyl, guanidinohexyl, carbamimidoyl, aminomethylcyclohexylmethyl, aminopropoxypropyl, aminocyclohexyl, hydroxyhexyl, dihydroxypropyl, aminomethylphenylmethyl, guanidinomethylphenylmethyl, phenylmethyl, morpholinopropyl, piperidinyl, hexyl, pyridinylethyl, allyl, amido-benzyl, aminopropyl-amidobenzyl, (2-amino)-amidoethyl-benzyl, (2-amino)-dimethylamidoethyl-benzyl, 2-amino-1-aminomethyl-ethyl, 5-amino-5-ethoxycarbonyl-pentyl, aminomethylphenylpropyl, aminomethylphenyl, aminophenymethyl, aminoethoxyphenylmethyl, aminomethyl-fluorophenyl-methyl, or aminomethyl-difluorophenyl-methyl, and $R_4$ is H, $(C_{1-4})$alkylcarbonyl, or aminomethylphenylcarbonyl or a pharmaceutically acceptable salt or solvate, prodrug or metabolite thereof.

16. The method according to claim 8, wherein, in the compound or the pharmaceutically acceptable salt or solvate thereof, $R_1$ is aminomethylphenylpropyl, aminoethylaminomethylphenylethenyl, aminoethylaminomethylphenylethyl, aminomethylphenylethyl, aminomethylphenylethyl, pyridinylethenyl, or aminoethylamino-fluorophenyl-ethenyl.

17. The method according to claim 8, wherein the compound or the pharmaceutically acceptable salt or solvate thereof is selected from 12-epi-12-desvinyl-14-O-{{4-[(3-Amino-propylcarbamoyl)-methyl]-phenylsulfanyl}-acetyl}-12-[(3-amino-propylamino)-methyl]mutilin, 12-epi-12-desvinyl-14-O-{{4-[(2-Amino-ethylcarbamoyl)-methyl]-phenylsulfanyl}-acetyl}-12-[(3-amino-propylamino)-methyl]mutilin, 12-epi-12-desvinyl-14-O-{{4-([Bis-(3-amino-propyl)-carbamoyl]-methyl}-phenylsulfanyl)-acetyl}-12-[(3-amino-propylamino)-methyl]mutilin, 12-epi-12-desvinyl-14-O-{{4-[(2,3-Diamino-propylcarbamoyl)-methyl]-phenylsulfanyl}-acetyl}-12-[(3-amino-propylamino)-methyl]mutilin, 12-epi-12-desvinyl-14-O-{{4-[(2-Amino-ethylcarbamoyl)-methyl]-phenylsulfanyl}-acetyl}-12-[(2-amino-ethylamino)-methyl]mutilin, 12-epi-12-desvinyl-14-O-{{4-[(3-Amino-propylcarbamoyl)-methyl]-phenylsulfanyl}-acetyl}-12-[(2-amino-ethylamino)-methyl]mutilin, 12-epi-12-desvinyl-14-O-{{4-[(3-Amino-propylcarbamoyl)-methyl]-phenylsulfanyl}-acetyl}-12-[(4-amino-butylamino)-methyl]mutilin, 12-epi-12-desvinyl-14-O-{{4-[(3-Amino-propylcarbamoyl)-methyl]-phenylsulfanyl}-acetyl}-12-[(5-amino-pentylamino)-methyl]mutilin, 12-epi-12-desvinyl-14-O-{{4-[(3-Amino-propylcarbamoyl)-methyl]-phenylsulfanyl}-acetyl}-12-[(4-aminomethyl-benzylamino)-methyl]mutilin, 12-epi-12-desvinyl-14-O-{{4-[(3-Amino-propylcarbamoyl)-methyl]-phenylsulfanyl}-acetyl}-12-[(6-amino-hexylamino)-methyl]mutilin, 12-epi-12-desvinyl-14-O-{{4-[(3-Amino-propylcarbamoyl)-methyl]-phenylsulfanyl}-acetyl}-12-[(6-guanidino-hexylamino)-methyl]mutilin, 12-epi-12-desvinyl-14-O-{{4-[(3-Amino-propylcarbamoyl)-methyl]-phenylsulfanyl}-acetyl}-12-[(4-guanidino-butylamino)-methyl]mutilin, 12-epi-12-desvinyl-14-O-{{4-[(3-Amino-propylcarbamoyl)-methyl]-phenylsulfanyl}-acetyl}-12-[(allylamino)-methyl]mutilin, 12-epi-12-desvinyl-14-O-{{4-[(3-Amino-propylcarbamoyl)-methyl]-phenylsulfanyl}-acetyl}-12-aminomethyl mutilin, 12-epi-12-desvinyl-14-O-{{4-[(3-Amino-propylcarbamoyl)-methyl]-phenylsulfanyl}-acetyl}-12-[(benzylamino)-methyl]mutilin, 12-epi-12-desvinyl-14-O-{{4-[(3-Amino-propylcarbamoyl)-methyl]-phenylsulfanyl}-acetyl}-12-[(4-guanidinomethyl-benzylamino)-methyl]mutilin, 12-epi-12-desvinyl-14-O-{{4-[(3-Amino-propylcarbamoyl)-methyl]-phenylsulfanyl}-acetyl}-12-[(6-hydroxy-hexylamino)-methyl]mutilin, 12-epi-12-desvinyl-14-O-{{4-[(3-Amino-propylcarbamoyl)-methyl]-phenylsulfanyl}-acetyl}-12-[(2,3-dihydroxypropylamino)-methyl]mutilin, 12-epi-12-desvinyl-14-O-{{4-[(3-Amino-propylcarbamoyl)-methyl]-phenylsulfanyl}-acetyl}-12-[(4-piperidylamino)-methyl]mutilin, 12-epi-12-desvinyl-14-O-{{4-[(3-Amino-propylcarbamoyl)-methyl]-phenylsulfanyl}-acetyl}-12-[(3-morpholin-4-yl-propylamino)-methyl]mutilin, 12-epi-12-desvinyl-14-O-{{4-[(3-Amino-propylcarbamoyl)-methyl]-phenylsulfanyl}-acetyl}-12-[(3-dimethylamino-propylamino)-methyl]mutilin, 12-epi-12-desvinyl-14-O-{{4-[(3-Amino-propylcarbamoyl)-methyl]-phenylsulfanyl}-acetyl}-12-[(S)-5-amino-5-ethoxycarbonyl-pentylamino-methyl]mutilin, 12-epi-12-desvinyl-14-O-{[4-(4-Aminomethyl-benzylcarbamoyl)-phenylsulfanyl]-acetyl}-12-[(6-amino-hexylamino)-methyl]mutilin, 12-epi-12-desvinyl-14-O-{[4-(4-Aminomethylbenzylcarbamoyl)-phenylsulfanyl]-acetyl}-12-[(6-guanidino-hexylamino)-methyl]mutilin, 12-epi-12-desvinyl-14-O-{[(4-Piperazinylcarbamoyl)-phenylsulfanyl]-acetyl}-12-[(6-guanidino-hexylamino)-methyl]mutilin, 12-epi-12-desvinyl-14-O-{[4-(4-Aminomethyl-piperidine-1-carbonyl)-phenylsulfanyl]-acetyl}-12-[(6-guanidino-hexylamino)-methyl]mutilin, 12-epi-12-desvinyl-14-O-{(4-[(Piperidin-4-ylmethyl)-carbamoyl]-phenylsulfanyl)-acetyl}-12-[(6-guanidino-hexylamino)-methyl]mutilin, 12-epi-12-desvinyl-14-O-{(4-[(Pyridin-4-ylmethyl)-carbamoyl]-phenylsulfanyl)-acetyl}-12-[(6-amino-hexylamino)-methyl]mutilin, 12-epi-12-desvinyl-14-O-{[3-(3-Aminopropylcarbamoyl)-phenylsulfanyl]-acetyl}-12-[(6-guanidino-hexylamino)-methyl]mutilin, 12-epi-12-desvinyl-14-O-{[4-(3-Acetylamino-propylcarbamoyl)-phenylsulfanyl]-acetyl}-12-[(3-amino-propylamino)-methyl]mutilin, 12-epi-12-desvinyl-14-O-{[4-(3-Formylamino-propylcarbamoyl)-phenylsulfanyl]-acetyl}-12-[(3-amino-propylamino)-methyl]mutilin, 12-epi-12-desvinyl-14-O-{[4-(3-Amino-propylcarbamoyl)-phenylsulfanyl]-acetyl}-12-[(3-amino-propylamino)-methyl]mutilin, 12-epi-12-desvinyl-14-O-{(4-[(3-Aminopropylcarbamoyl)-phenylsulfanyl)-acetyl}-12-[(4-aminomethyl-benzylamino)-methyl]mutilin, 12-epi-12-desvinyl-14-O-{(4-[(3-Aminopropylcarbamoyl)-phenylsulfanyl)-acetyl}-12-[(6-amino-hexylamino)-methyl]mutilin, 12-epi-12-desvinyl-14-O-{[4-(3-Aminopropylcarbamoyl)-phenylsulfanyl]-acetyl}-12-[(6-guanidino-hexylamino)-methyl]mutilin, 12-epi-12-desvinyl-14-O-{[4-(3-Aminopropylcarbamoyl)-phenylsulfanyl]-acetyl}-12-[(8-amino-octylamino)-methyl]mutilin, 12-epi-12-desvinyl-14-O-{[4-(3-Aminopropylcarbamoyl)-phenylsulfanyl]-acetyl}-12-[(10-amino-decylamino)-methyl]mutilin, 12-epi-12-desvinyl-14-O-{(4-Carbamoyl-phenylsulfanyl)-acetyl}-12-[(6-guanidino-hexylamino)-methyl]mutilin, 12-epi-12-desvinyl-14-O-{[4-(3-Amino-propylcarbamoyl)-phenylsulfanyl]-acetyl}-12-{[3-(3-amino-propoxy)-propylamino)]-methyl}mutilin, 12-epi-12-desvinyl-14-O-{[4-(3-Amino-propylcarbamoyl)-phenylsulfanyl]-acetyl}-12 [(2-pyridin-4-yl-ethylamino)-methyl]mutilin, 12-epi-12-desvinyl-14-O-{[4-(6-Amino-hexylcarbamoyl)-phenylsulfanyl]-acetyl}-12-[(6-guanidino-hexylamino)-methyl]mutilin, 12-epi-12-desvinyl-14-O-{[4-(2-Amino-ethylcarbamoyl)-phenylsulfanyl]-acetyl}-12-[(6-guanidino-hexylamino)-methyl]mutilin, 12-epi-12-desvinyl-14-O-{[4-(3-Aminopropylcarbamoyl)-phenylsulfanyl]-acetyl}-12-{[3-(4-aminomethyl-phenyl)-propylamino]-methyl}mutilin, 12-epi-12-desvinyl-14-O-{[(4-Aminomethyl-cyclohexyl)-methylsulfanyl]-acetyl}-12-[(6-amino-hexylamino)-methyl]mutilin, 12-epi-14-O-[(1-Methyl-piperidin-4-ylsulfanyl)-acetyl}-12-[(6-guanidino-hexylamino)-methyl]mutilin, 12-epi-14-O-[(Piperidin-4-ylsulfanyl)-acetyl]-12-[(6-amino-hexylamino)-methyl]mutilin, 12-epi-12-desvinyl-14-O-{[(4-Aminomethyl-cyclohexyl)-sulfanyl]-acetyl}-12-[(6-amino-hexylamino)-methyl]mutilin, 12-epi-12-desvinyl-14-O-{[4-(3-Amino-propyl)-phenylsulfanyl]-acetyl}-12-[(6-amino-hexylamino)-methyl]mutilin, 12-epi-12-desvinyl-14-O-{(4-[(3-Amino-propylcarbamoyl)-methyl]-phenylsulfanyl)-acetyl}-12-{[(3-amino-propyl)-acetylamino]-methyl}mutilin, 12-epi-12-desvinyl-14-O-{(4-[(3-Amino-propylcarbamoyl)-methyl]-phenylsulfanyl)-acetyl}-12-(3-amino-propylcarbamoyl) mutilin, 12-epi-12-desvinyl-14-O-{[4-(3-Amino-propylcarbamoyl)-phenylsulfanyl]-acetyl}-12-(4-aminomethyl-benzylcarbamoyl) mutilin, 12-epi-12-desvinyl-14-O-{{4-[(3-Amino-propylcarbamoyl)-methyl]-phenylsulfanyl}-acetyl}-12-[2-(3-amino-propylamino)-ethyl]mutilin, 12-epi-12-desvinyl-14-O-[(3-Hydroxymethyl-phenylsulfanyl)-acetyl]-12-[(3-amino-propylamino)-methyl] mutilin, 12-epi-12-desvinyl-14-O-[(3-Hydroxymethyl-phenylsulfanyl)-acetyl]-12-[(6-amino-hexylamino)-methyl] mutilin, 12-epi-12-desvinyl-14-O-[(3-Hydroxymethyl-phenylsulfanyl)-acetyl]-12-[(4-aminomethyl-benzylamino)-methyl]mutilin, 12-epi-12-desvinyl-14-O-[(3-Hydroxymethyl-phenylsulfanyl)-acetyl]-12-[(6-guanidino-hexylamino)-methyl] mutilin, 12-epi-12-desvinyl-14-O-[(4-Hydroxymethyl-phenylsulfanyl)-acetyl]-12-[(3-amino-propylamino)-methyl] mutilin, 12-epi-12-desvinyl-14-O-[(4-Hydroxymethyl-phenylsulfanyl)-acetyl]-12-[(4-aminomethyl-benzylamino)-methyl]mutilin, 12-epi-12-desvinyl-14-O-[(4-Hydroxymethyl-phenylsulfanyl)-acetyl]-12-[(6-amino-hexylamino)-methyl] mutilin, 12-epi-12-desvinyl-14-O-[(3,5-Bis-hydroxymethyl-phenylsulfanyl)-acetyl]-12-[(3-amino-propylamino)-methyl]mutilin, 12-epi-12-desvinyl-14-O-{[(2,3,5,6-Tetrafluoro-4-hydroxymethyl)-phenylsulfanyl]-acetyl}-12-[(4-aminomethyl-benzylamino)-methyl]-mutilin, 12-epi-12-desvinyl-14-O-{[(1R,2R,4R)-4-Amino-2-hydroxy-cyclohexylsulfanyl]-acetyl}-12-[(3-amino-propylamino)-methyl]mutilin, 12-epi-12-desvinyl-14-O-{[(1R,2R,4R)-4-Amino-2-hydroxy-cyclohexylsulfanyl]-acetyl}-12-[(4-aminomethyl-benzylamino)-methyl]mutilin, 12-epi-12-desvinyl-14-O-[(2-Hydroxy-ethylsulfanyl)-acetyl]-12-[(4-aminomethyl-benzylamino)-methyl] mutilin, 12-epi-12-desvinyl-14-O-[(2-Amino-ethylsulfanyl)-acetyl]-12-[(4-aminomethyl-benzylamino)-methyl] mutilin, 12-epi-12-desvinyl-14-O-{[(5-Amino-4H-1,2,4-triazol-3-yl)-sulfanyl]-acetyl}-12-[(6-amino-hexylamino)-methyl]mutilin, 12-epi-12-desvinyl-14-O-[(2-Amino-ethylsulfanyl)-acetyl]-12-[(6-amino-hexylamino)-methyl]mutilin, 12-epi-12-desvinyl-14-O-[(Pyridin-4-ylsulfanyl)-acetyl]-12-[(6-amino-hexylamino)-methyl]mutilin, 12-epi-12-desvinyl-14-O-[(Pyridin-4-ylsulfanyl)-acetyl]-12-[(6-guanidino-hexylamino)-methyl]mutilin, 12-epi-12-desvinyl-14-O-[(3-Hydroxy-phenylsulfanyl)-acetyl]-12-[(6-amino-hexylamino)-methyl]mutilin, 12-epi-12-desvinyl-14-O-[(4-Fluoro-phenylsulfanyl)-acetyl]-12-[(6-amino-hexylamino)-methyl]mutilin, 12-epi-12-desvinyl-14-O-{[(7H-Purin-6-yl)-sulfanyl]-acetyl}-12-[(6-amino-hexylamino)-methyl]mutilin, 12-epi-12-desvinyl-14-O-[(3-Amino-phenylsulfanyl)-acetyl]-12-[(3-amino-propylamino)-methyl]mutilin, 12-epi-12-desvinyl-14-O-(Phenylsulfanyl-acetyl)-12-[(4-aminomethyl-benzylamino)-methyl]mutilin, 12-epi-12-desvinyl-14-O-[(4-Fluoro-phenylsulfanyl)-acetyl]-12-[(4-aminomethyl-benzylamino)-methyl] mutilin, 12-epi-12-desvinyl-14-O-[(Pyridin-2-ylsulfanyl)-acetyl]-12-[(4-aminomethyl-benzylamino)-methyl]mutilin, 12-epi-12-desvinyl-14-O-[(Pyridin-4-ylsulfanyl)-acetyl]-12-[(4-aminomethyl-benzylamino)-methyl]mutilin, 12-epi-12-desvinyl-14-O-{[1-(2-Amino-acetyl)-piperidin-4-yl-sulfanyl)]-acetyl}-12-[(4-aminomethyl-benzylamino)-methyl]mutilin, 12-epi-12-desvinyl-14-O-{[1-(3-Amino-propionyl)-piperidin-4-yl-sulfanyl)]-acetyl}-12-[(4-aminomethyl-benzylamino)-methyl]mutilin, 12-epi-12-desvinyl-14-O-{[1-(3-Amino-propionyl)-piperidin-4-yl-sulfanyl]-acetyl}-12-[(6-amino-hexylamino)-methyl]mutilin, 12-epi-12-desvinyl-14-O-{[1-(2-Amino-acetyl)-piperidin-4-yl-methylsulfanyl]-acetyl}-12-[(4-aminomethyl-phenylamino)-methyl]mutilin, 12-epi-12-desvinyl-14-O-{[1-(2-Amino-acetyl)-piperidin-4-yl-methylsulfanyl]-acetyl}-12-[(4-amino-benzylamino)-methyl]mutilin, 12-epi-12-desvinyl-14-O-{[1-(2-Amino-acetyl)-piperidin-4-yl-sulfanyl]-acetyl}-12 {2-[4-(2-amino-ethoxy)-benzylamino]-methyl}mutilin, 12-epi-12-desvinyl-14-O-{{4-[(2-Amino-acetylamino)-methyl]-cyclohexylsulfanyl}-acetyl}-12-[{4-[(2-amino-ethoxy)-benzylamino]-methyl}mutilin, 12-epi-12-desvinyl-14-O-[(4-Aminomethyl-phenylsulfanyl)-acetyl]-12-[(3-amino-propylamino)-methyl]mutilin, 12-epi-12-desvinyl-14-O-[(3-Aminomethyl-phenylsulfanyl)-acetyl]-12-[(3-amino-propylamino)-methyl]mutilin, 12-epi-12-desvinyl-14-O-[(3-Aminomethyl-phenylsulfanyl)-acetyl]-12-[(6-guanidino-hexylamino)-methyl] mutilin, 12-epi-12-desvinyl-14-O-[(4-Aminomethyl-phenylsulfanyl)-acetyl]-12-[(4-aminomethyl-benzylamino)-methyl]mutilin, 12-epi-12-desvinyl-14-O-[(4-Aminomethyl-phenylsulfanyl)-acetyl]-12-[(6-amino-hexylamino)-methyl]mutilin, 12-epi-12-desvinyl-14-O-[(3-Aminomethyl-phenylsulfanyl)-acetyl]-12-[((4-aminomethyl-cyclohexyl)-methyl-amino)-methyl]mutilin, 12-epi-12-desvinyl-14-O-[(4-Aminomethyl-phenylsulfanyl)-acetyl]-12-{[(4-aminocyclohexyl)-amino]-methyl}mutilin, 12-epi-12-desvinyl-14-O-[(4-Aminomethyl-phenylsulfanyl)-acetyl]-12-[(hexylamino)-methyl]mutilin, 12-epi-12-desvinyl-14-O-[(4-Aminomethyl-phenylsulfanyl)-acetyl]-12-[(4-carbamoylphenyl)-methylamino)-methyl]mutilin, 12-epi-12-desvinyl-14-O-[(4-Aminomethyl-phenylsulfanyl)-acetyl]-12-{[4-(3-amino-propylcarbamoyl)-benzylamino]-methyl}mutilin, 12-epi-12-desvinyl-14-O-[(4-Aminomethyl-phenylsulfanyl)-acetyl]-12-[(5-dimethylcarbamoyl-pentylamino)-methyl]mutilin, 12-epi-12-desvinyl-14-O-[(4-Aminomethyl-phenylsulfanyl)-acetyl]-12-{[4-(2-amino-2-carbamoyl-ethyl)-benzylamino]-methyl}mutilin, 12-epi-12-desvinyl-14-O-[(4-Aminomethyl-phenylsulfanyl)-acetyl]-12-{[4-(2-amino-2-dimethylcarbamoyl-ethyl)-benzylamino]-methyl}mutilin, 12-epi-12-desvinyl-14-O-{[5-Aminomethyl-pyridin-2-yl-sulfanyl)]-acetyl}-12-[(4-aminomethyl-benzylamino)-methyl]mutilin, 12-epi-12-Desvinyl-14-O-{[5-aminomethyl-pyridin-2-yl-sulfanyl)]-acetyl}-12-[(4-aminomethyl-3-fluoro-benzylamino)-methyl]mutilin, 12-epi-12-desvinyl-14-O-{[(4-Aminomethyl-cyclohexyl)-methylsulfanyl)-acetyl]{[(4-Aminomethyl-cyclohexyl)-methylsulfanyl]-acetyl}-12-[(4-aminomethyl-benzylamino)-methyl]mutilin, 12-epi-12-desvinyl-14-O-{1-(2-Amino-acetyl)-piperidin-4-yl-sulfanyl]-acetyl}-12-[(4-aminomethyl-3-fluoro-benzylamino)-methyl]mutilin, 12-epi-12-Desvinyl-14-O-{{4-[(2-Amino-acetylamino)-methyl]-cyclohexylsulfanyl}-acetyl}-12-[(4-aminomethyl-3-fluoro-benzylamino)-methyl]mutilin, 12-epi-12-desvinyl-14-O-{[5-Aminomethyl-pyridin-2-yl-sulfanyl]-acetyl}-12-[(4-aminomethyl-2,5-difluoro-benzylamino)-methyl]mutilin, 12-epi-12-desvinyl-14-O-[(4-Aminomethyl-phenylsulfanyl)-acetyl]-12-[(2-amino-1-aminomethyl-ethyl-amino)-methyl]mutilin, 12-epi-12-Desvinyl-14-O-[(5-aminomethyl-pyridin-2-yl-sulfanyl)-acetyl]-12-[(6-amino-hexylamino)-methyl] mutilin, 12-epi-12-desvinyl-14-O-{(4-[(2-Amino-acetylamino)-methyl]-phenylsulfanyl)-acetyl}-12-[(3-amino-propylamino)-methyl]mutilin, 12-epi-12-desvinyl-14-O-{(4-[(2-Amino-3-(4-hydroxy-phenyl)-propionylamino)-methyl]-phenylsulfanyl)-acetyl}-12-[(3-amino-propylamino)-methyl]mutilin, 12-epi-12-desvinyl-14-O-{(4-[(3-Amino-propionylamino)-methyl]-phenylsulfanyl)-acetyl}-12-[(3-amino-propylamino)-methyl]mutilin, 12-epi-12-desvinyl-14-O-{(4-[(2-Amino-acetylamino)-methyl]-phenylsulfanyl)-acetyl}-12-[4-aminomethyl-benzylamino-methyl]mutilin, 12-epi-12-desvinyl-14-O-{(4-[(2-Amino-acetylamino)-methyl]-phenylsulfanyl)-acetyl}-12-(6-amino-hexylamino-methyl) mutilin, 12-epi-12-desvinyl-14-O-{[(3-Acetylamino-methyl)-phenylsulfanyl]-acetyl}-12-[(3-amino-propylamino)-methyl]mutilin, 12-epi-12-desvinyl-14-O-{(4-{[2-Amino-3-(4-aminomethyl-phenyl)-propionylamino]-methyl}-phenylsulfanyl)-acetyl}-12-[(3-amino-propylamino)-methyl]mutilin, 12-epi-12-desvinyl-14-O-{{4-[(3-Amino-propylamino)-methyl]-phenylsulfanyl}-acetyl}-12-[(3-amino-propylamino)-methyl]mutilin, 12-epi-12-desvinyl-14-O-{{3-[(3-Amino-propylamino)-methyl]-phenylsulfanyl}-acetyl}-12-[(3-amino-propylamino)-methyl]mutilin, 12-epi-12-desvinyl-14-O-{{4-[(4-Aminomethyl-benzylamino)-methyl]-phenylsulfanyl}-acetyl}-12-[(3-amino-propylamino)-methyl]mutilin, 12-epi-12-desvinyl-14-O-[(3-Allylaminomethyl-phenylsulfanyl)-acetyl]-12-[(3-amino-propylamino)-methyl]mutilin, 12-epi-12-desvinyl-14-O-{{4-[(3-Amino-propylamino)-methyl]-phenylsulfanyl}-acetyl}-12-{[3-(3-amino-propoxy)-propylamino]-methyl}mutilin,
12-epi-12-desvinyl-14-O-[(4-Cyclopropylaminomethyl-phenylsulfanyl)-acetyl]-12-[(3-amino-propylamino)-methyl]mutilin,
12-epi-12-desvinyl-14-O-[(4-Cyclopropylaminomethyl-phenylsulfanyl)-acetyl]-12-[(6-amino-hexylamino)-methyl]mutilin,
12-epi-12-desvinyl-14-O-{{4-[(4-Aminomethyl-benzylamino)-methyl]-phenylsulfanyl}-acetyl}-12-[(6-amino-hexylamino)-methyl]mutilin,
12-epi-12-desvinyl-14-O-{{4-[(4-Aminomethyl-benzylamino)-methyl]-phenylsulfanyl}-acetyl}-12-[(4-aminomethyl-benzylamino)-methyl]-mutilin,
12-epi-12-desvinyl-14-O-[5-(3-Amino-propylcarbamoyl)-pyridin-2-ylsulfanyl]-acetyl-12-[(6-amino-hexylamino)-methyl]mutilin,
12-epi-12-desvinyl-14-O-[(2,5-Bis-aminomethyl-phenylsulfanyl)-acetyl]-12-[(3-amino-propylamino)-methyl]mutilin,
12-epi-12-desvinyl-14-O-[(3,5-Bis-aminomethyl-phenylsulfanyl)-acetyl]-12-[(3-amino-propylamino)-methyl]mutilin,
12-epi-12-desvinyl-14-O-{[(3-Amino-propylcarbamoyl)-phenylsulfanyl]-acetyl}-12-[(2-guanidino-ethyl]mutilin,
12-epi-12-desvinyl-14-O-{[4-(3-Hydroxy-propylcarbamoyl)-phenylsulfanyl]-acetyl}-12-[(6-amino-hexylamino)-methyl]mutilin,
12-epi-12-desvinyl-14-O-[(2-Hydroxy-ethylsulfanyl)-acetyl]-12-[(6-amino-hexylamino)-methyl]mutilin,
12-epi-12-desvinyl-14-O-{[3-(2,2-Difluoro-ethylamino)-cyclohexylsulfanyl]-acetyl}-12-[(6-amino-hexylamino)-methyl]mutilin,
12-epi-12-desvinyl-14-O-[(2-Amino-7H-purin-6-ylsulfanyl)-acetyl]-12-[(6-amino-hexylamino)-methyl]mutilin,
12-epi-12-desvinyl-14-O-[(Azepan-4-ylsulfanyl)-acetyl]-12-[(6-amino-hexylamino)-methyl]mutilin,
12-epi-12-desvinyl-14-O-[(Azepan-4-ylsulfanyl)-acetyl]-12-[(6-guanidino-hexylamino)-methyl]mutilin,
12-epi-12-desvinyl-14-O-[(Azepan-4-ylsulfanyl)-acetyl]-12-[(4-aminomethyl-benzylamino)-methyl]mutilin,
12-epi-12-desvinyl-14-O-[(Azepan-4-ylsulfanyl)-acetyl]-12-[(6-amino-octylamino)-methyl]mutilin,
12-epi-12-desvinyl-14-O-{[1-(2-Amino-acetyl)-piperidin-4-yl-sulfanyl)]-acetyl}-12-[(6-amino-hexylamino)-ethyl]mutilin,
12-epi-12-desvinyl-14-O-{[1-(2-Amino-acetyl)-piperidin-4-yl-sulfanyl)]-acetyl}-12-[(4-aminomethyl-benzylamino)-ethyl]mutilin,
12-epi-12-desvinyl-14-O-[5-Hydroxymethyl-pyridin-2-yl-sulfanylacetyl]-12-[(4-aminomethyl-3-fluoro-benzylamino)-ethyl]mutilin,
12-epi-12-desvinyl-14-O-{4-[(2-Amino-acetylamino)-cyclohexylsulfanyl]-acetyl}-12-[(4-aminomethyl-3-fluoro-benzylamino)-ethyl]mutilin,
12-epi-12-desvinyl-14-O-{[1-(2-Amino-acetyl)-piperidin-4-yl-sulfanyl]-acetyl}-12-[(4-aminomethyl-3-fluoro-benzylamino)-ethyl]mutilin,
12-epi-12-desvinyl-14-O-[(5-Aminomethyl-pyridin-2-yl-sulfanyl)-acetyl]-12-[(4-aminomethyl-2,5-difluoro-benzylamino)-ethyl]mutilin,
12-epi-12-desvinyl-14-O-{[1-(2-Amino-acetyl)-piperidin-4-yl-sulfanyl]-acetyl}-12-[(4-aminomethyl-2,5-difluoro-benzylamino)-ethyl]mutilin,
12-epi-12-desvinyl-14-O-{[1-(2-Amino-acetyl)-piperidin-4-yl-sulfanyl]-acetyl}-12 {2-[4-(2-amino-ethoxy)-benzylamino]-ethyl}mutilin,
12-epi-12-desvinyl-14-O-{{4-[(2-Amino-acetylamino)-methyl]-cyclohexylsulfanyl}-acetyl}-12-[(4-aminomethyl-3-fluoro-benzylamino)-ethyl]mutilin,
12-epi-12-desvinyl-14-O-[(Azepan-4-ylsulfanyl)-acetyl]-12-[(4-aminomethyl-phenylamino)-ethyl]mutilin,
12-epi-12-desvinyl-14-O-{{4-[(2-Amino-acetylamino)]-cyclohexylsulfanyl}-acetyl}-12-[(4-aminomethyl-phenylamino)-ethyl]mutilin,
12-epi-12-desvinyl-14-O-{[1-(2-Amino-acetyl)-piperidin-4-yl-methylsulfanyl]-acetyl}-12-[(4-aminomethyl-phenylamino)-ethyl]mutilin,
12-epi-12-desvinyl-14-O-{[1-(2-Amino-acetyl)-piperidin-4-yl-sulfanyl]-acetyl}-12-(8-amino-octyl) mutilin,
12-epi-12-desvinyl-14-O-{[1-(2-Amino-acetyl)-piperidin-4-yl-sulfanyl]-acetyl}-12-[3-(4-aminomethyl-phenyl)-propyl]mutilin,
12-epi-12-desvinyl-14-O-[(Azepan-4-yl-sulfanyl)-acetyl]-12-[3-(4-aminomethyl-phenyl)-propyl]mutilin,
12-epi-12-desvinyl-14-O-[(Azepan-4-yl-sulfanyl)-acetyl]-12-(6-aminohexyl) mutilin,
12-epi-12-desvinyl-14-O-[(Azepan-4-yl-sulfanyl)-acetyl]-12-(8-amino-octyl) mutilin,
12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethenyl) mutilin,
12-epi-12-desvinyl-14-O-{{4-[(2-Amino-acetylamino)-methyl]-cyclohexylsulfanyl}-acetyl}-12-[2-{4-[(2-amino-ethylamino)-methyl]-phenyl}-ethyl) mutilin,
12-epi-12-desvinyl-14-O-[(Azepan-4-ylsulfanyl)-acetyl]-12-[2-(4-Aminomethyl-phenyl)-ethyl]-mutilin,
12-epi-12-desvinyl-14-O-[(Azepan-4-ylsulfanyl)-acetyl]-12-((E)-2-pyridin-3-yl-ethenyl) mutilin,
12-epi-12-desvinyl-14-O-[(Azepan-4-ylsulfanyl)-acetyl]-12-((E)-2-{4-[(2-Amino-ethylamino)-methyl]-phenyl}-ethenyl) mutilin,
12-epi-12-desvinyl-14-O-[(Azepan-4-ylsulfanyl)-acetyl]-12-[2-{4-[(2-amino-ethylamino)-methyl]-phenyl}-ethyl) mutilin,
12-epi-12-desvinyl-14-O-[(Azepan-4-ylsulfanyl)-acetyl]-12-((E)-2-{4-[(2-amino-ethylamino)-methyl]-3-fluoro-phenyl}-ethenyl) mutilin,
12-epi-14-O-{[1-(2-Amino-acetyl)-piperidin-4-yl-sulfanyl]-acetyl}-12-((E)-2-{4-[(2-amino-ethylamino)-methyl]-phenyl}-ethenyl) mutilin,
12-epi-14-O-{[1-(2-Amino-acetyl)-piperidin-4-yl-sulfanyl]-acetyl}-12-[2-{4-[(2-amino-ethylamino)-methyl]-phenyl}-ethyl) mutilin,
12-epi-12-desvinyl-14-O-[(5-Aminomethyl-pyridin-2-ylsulfanyl)-acetyl]-12-[2-(4-aminomethyl-benzoylamino)-ethyl]mutilin,
12-epi-12-desvinyl-14-O-[(Piperidin-4-ylsulfanyl]-acetyl]-12-[2-(3-methyl-pyrazin-2-yl)-ethenyl]-mutilin, and their pharmaceutically acceptable salts or solvates.

18. The method according to claim 8, wherein the compound or the pharmaceutically acceptable salt or solvate thereof is 12-epi-12-desvinyl-14-O-[(Piperidin-4-ylsulfanyl]-acetyl]-12-[2-(3-methyl-pyrazin-2-yl)-ethenyl]-mutilin or its pharmaceutically acceptable salts or solvates.

19. The method according to claim 8, wherein the viral infection relates to a respiratory disease.

20. The method according to claim 8, wherein the viral infection relates to an acute respiratory syndrome optionally including Influenza, Severe Acute Respiratory Syndrome (SARS), Middle East Respiratory Syndrome (MERS) or COVID-19.

21. The method according to claim 8, the viral infection is associated with a virus being a positive- or negative-sense single-stranded RNA virus, optionally the virus is Coronaviridae, optionally including human coronavirus, Paramyxoviridae, optionally including Paramyxovirinae, optionally including Measles virus, or Pneumovirinae, optionally including Respiratory Syncytial Virus, Orthomyxoviridae, optionally including Influenza virus, Flaviviridae, optionally including Dengue virus or Zika virus, or Picornaviridae, optionally including Rhinovirus.

22. The method according to claim 8, wherein the viral infection relates to an airborne disease.

* * * * *